(12) United States Patent
Porat et al.

(10) Patent No.: US 8,273,312 B2
(45) Date of Patent: Sep. 25, 2012

(54) LIQUID TESTING ASSEMBLY

(75) Inventors: Gadi Porat, Jerusalem (IL); Joel Stern, Herzliya (IL); Boaz Rimon, Tel Aviv (IL); Yoram Cohen, Shoham (IL)

(73) Assignee: Association for Public Health, Jerusalem (IL)

( * ) Notice: Subject to any disclaimer, the term of this patent is extended or adjusted under 35 U.S.C. 154(b) by 512 days.

(21) Appl. No.: 12/524,010

(22) PCT Filed: Jan. 22, 2008

(86) PCT No.: PCT/IL2008/000099
§ 371 (c)(1),
(2), (4) Date: Jul. 22, 2009

(87) PCT Pub. No.: WO2008/090551
PCT Pub. Date: Jul. 31, 2008

(65) Prior Publication Data
US 2010/0079751 A1    Apr. 1, 2010

Related U.S. Application Data

(60) Provisional application No. 60/881,846, filed on Jan. 23, 2007, provisional application No. 60/960,634, filed on Oct. 9, 2007.

(51) Int. Cl.
*B01L 3/14* (2006.01)

(52) U.S. Cl. ........ 422/550; 422/547; 422/549; 422/561; 422/559; 422/560; 422/568; 422/68.1; 422/69; 422/73; 422/82; 435/287.1; 435/287.2; 435/287.3; 435/287.4; 435/288.1; 435/288.2; 435/288.5; 435/30; 435/305.1; 435/309.3; 435/31; 435/34; 435/40; 435/40.5; 435/7.21; 435/299.2; 435/304.2; 435/309.2; 436/177; 210/455; 210/643; 210/94; 215/306; 220/254.1; 356/300; 439/177; 600/572; 600/573; 600/577; 600/584; 604/416; 73/64.56; 73/863.52; 73/864.51; 73/864.52; 73/444

(58) Field of Classification Search .................. 422/102, 422/58, 61, 64, 68.1, 69, 73, 82, 547, 549, 422/550, 559, 560, 561, 568; 436/177; 435/287.1, 435/287.2, 287.3, 287.4, 288.1, 288.2, 288.5, 30, 305.1, 309.3, 31, 34, 40, 40.5, 7.21, 299.2, 304.2, 309.2; 210/455, 643, 94; 215/306; 220/254.1; 356/300; 439/177; 600/572, 573, 577, 584; 604/416; 73/444, 863.52, 864.52, 64.56, 864.51
See application file for complete search history.

(56) References Cited

U.S. PATENT DOCUMENTS 3,589,983 A    6/1971    Holderith et al.
(Continued)

FOREIGN PATENT DOCUMENTS

EP    0289761 A2    11/1988
(Continued)

OTHER PUBLICATIONS

P. Yagupsky et al., Clinical Evaluation of Novel Chromogenic Agar Dipslide for Diagnosis of Urinary Tract Infections, Eur J. Clin Microbiol Infect Dis. (2000) 19:694-698, pp. 5, © Springer-Verlag 2000.

(Continued)

*Primary Examiner* — Dennis M White
(74) *Attorney, Agent, or Firm* — Fleit Gibbons Gutman Bongini & Bianco; Paul D. Bianco; Martin Fleit

(57) ABSTRACT

A liquid testing assembly for testing a liquid, the assembly comprising a test vessel and a stopper adapted to fit into a free end of the vessel. The stopper substantially hermetically seals the test vessel from the ambient. Further, the assembly includes a support coated with one or more identifying materials for identifying one or more constituents of the liquid. The support is fixed in the stopper and/or the vessel and extends into its interior for a predetermined distance. The liquid testing assembly when assembled is pre-evacuated to a predetermined vacuum sufficient to draw a predetermined volume of liquid to be sampled into the test vessel. The predetermined volume is of such an amount that it wets the one or more identifying materials ensuring identification of one or more constituents present in the liquid. A kit employing the liquid testing assembly is also discussed.

20 Claims, 17 Drawing Sheets

U.S. PATENT DOCUMENTS

| | | | |
|---|---|---|---|
| 4,116,066 | A | 9/1978 | Mehl et al. |
| 4,300,404 | A | 11/1981 | Mehl et al. |
| 4,473,530 | A | 9/1984 | Villa-Real |
| 4,927,605 | A | 5/1990 | Dorn et al. |
| 5,051,238 | A | 9/1991 | Umetsu et al. |
| 5,420,018 | A | 5/1995 | Ricci |
| 5,763,264 | A * | 6/1998 | Alspector ............ 435/287.3 |
| 5,770,086 | A | 6/1998 | Indriksons et al. |
| 6,921,395 | B2 | 7/2005 | Carano et al. |
| 2004/0166023 | A1 | 8/2004 | Lappe et al. |

FOREIGN PATENT DOCUMENTS

| | | |
|---|---|---|
| EP | 0300221 A2 | 1/1989 |
| FR | 2888641 | 1/2007 |
| WO | 03/022435 A2 | 3/2003 |

OTHER PUBLICATIONS

International Search Report mailed Jul. 2, 2008 for PCT/IL2008/000099 filed Jan. 22, 2008.

Written Opinion of the International Searching Authority mailed Jul. 2, 2008 for PCT/IL2008/000099 filed Jan. 22, 2008.

\* cited by examiner

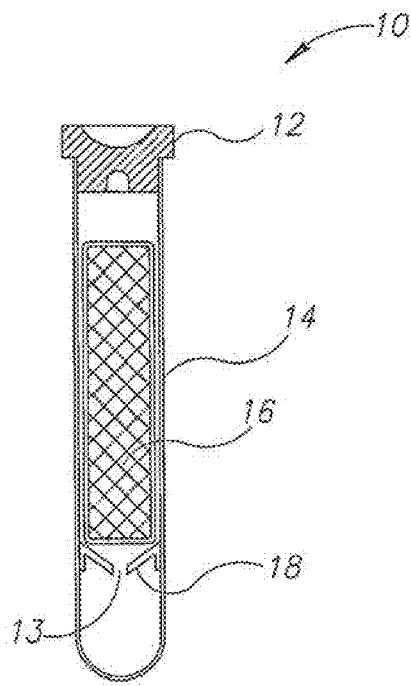
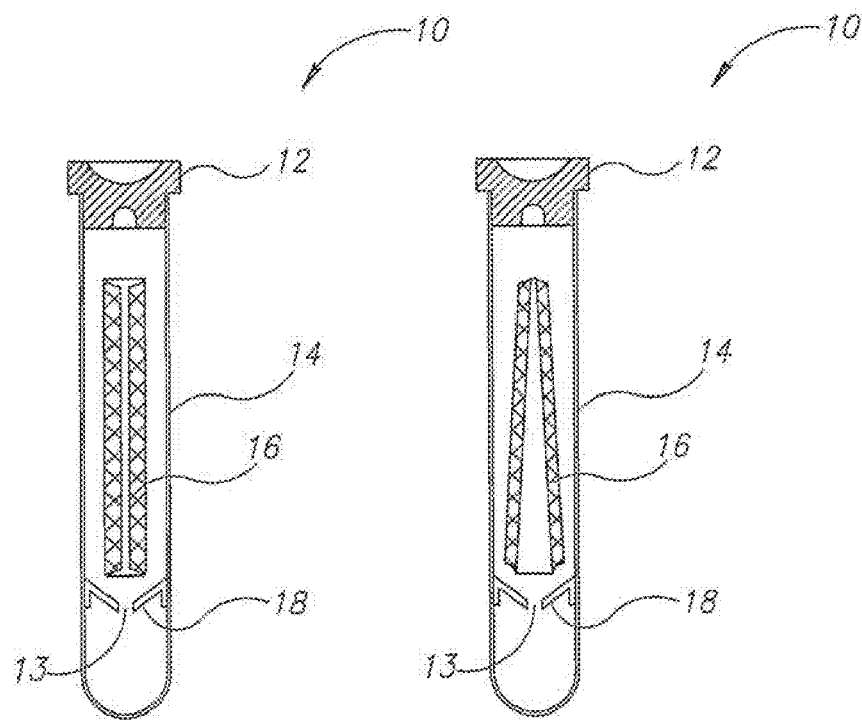
FIG.1A
FIG.1B  FIG.1C

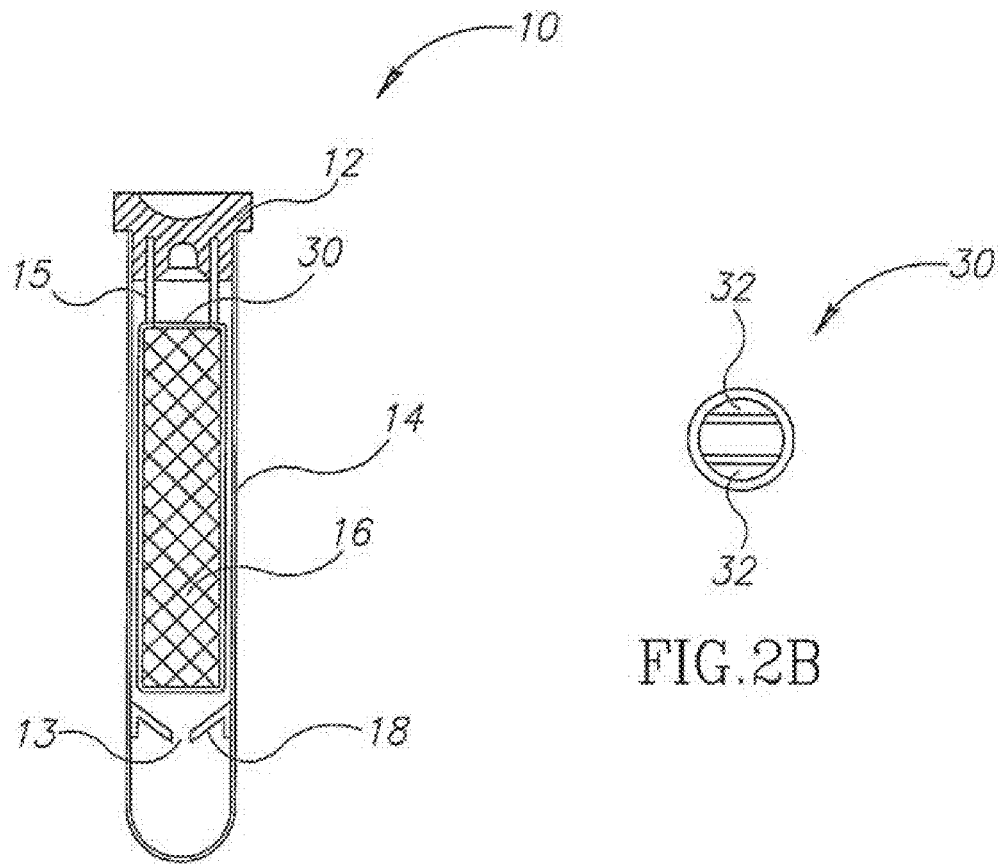
FIG.2A
FIG.2B
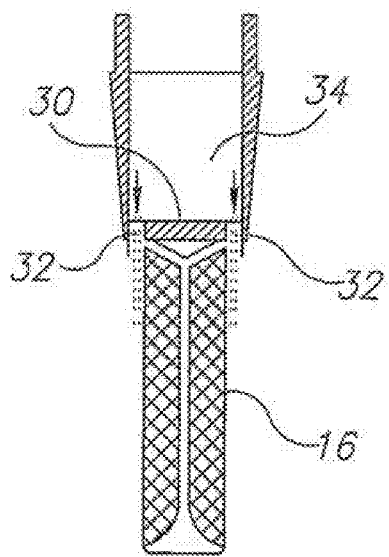
FIG.2C
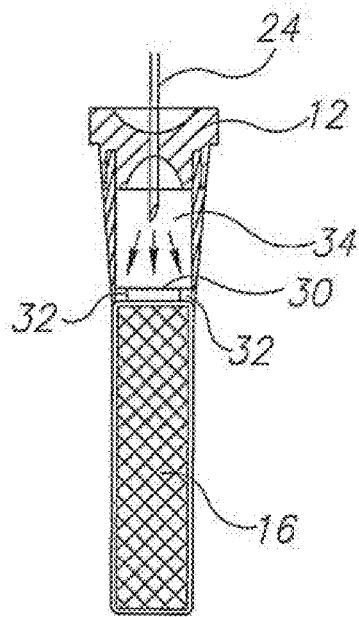
FIG.2D

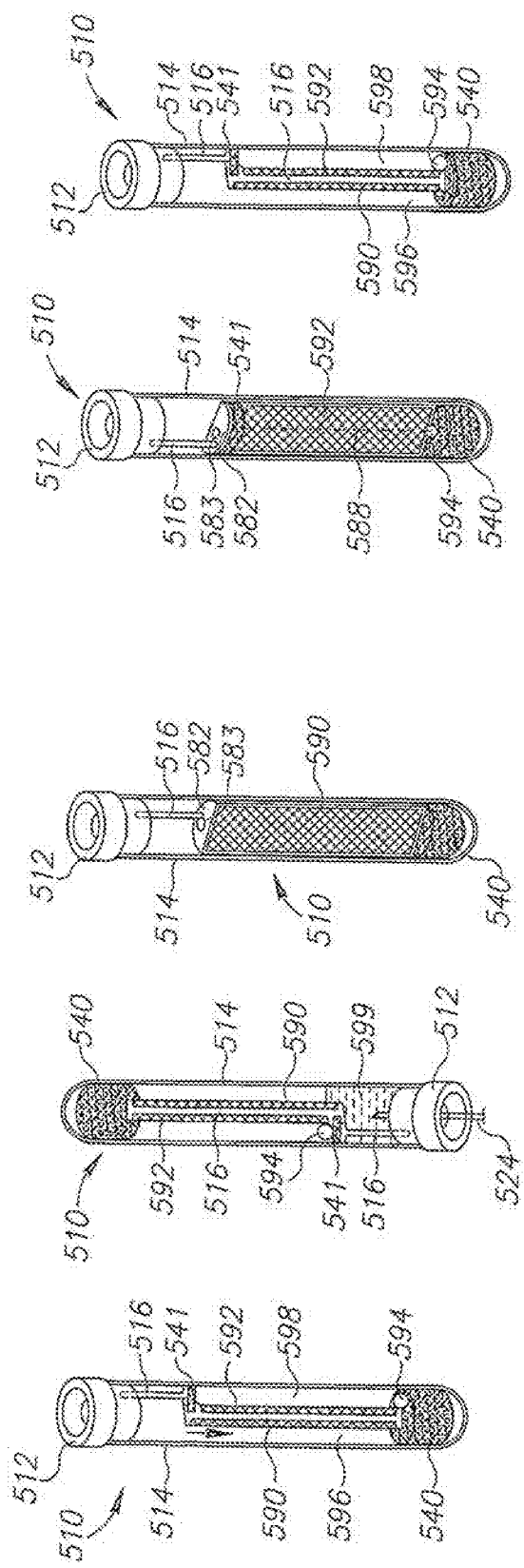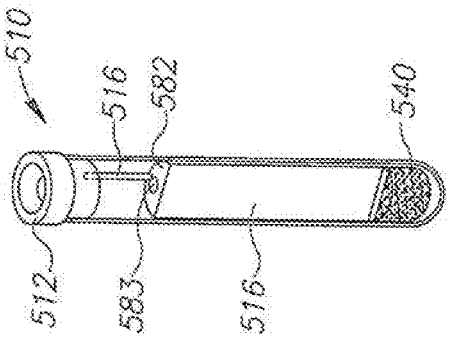

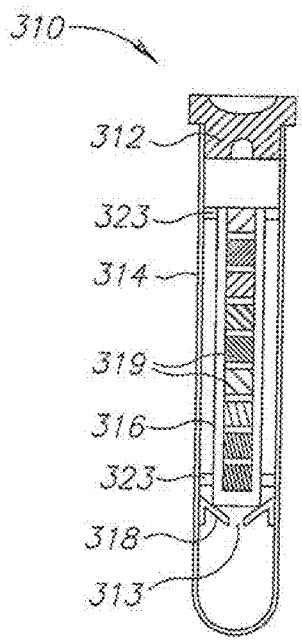
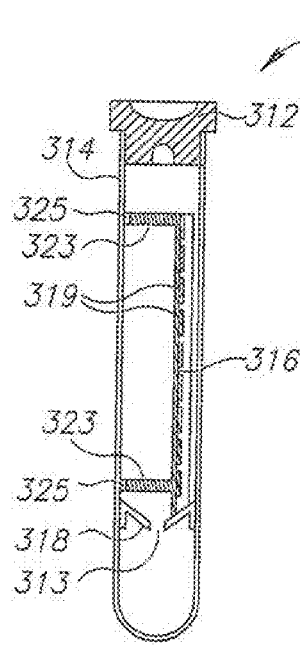
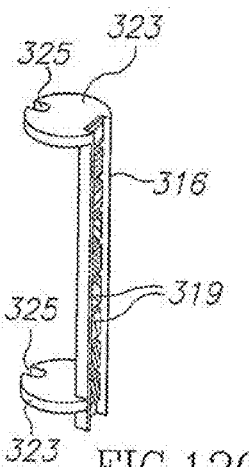
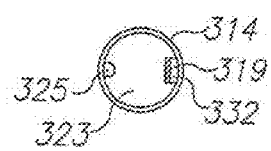
FIG.12A    FIG.12B    FIG.12C
FIG.12D
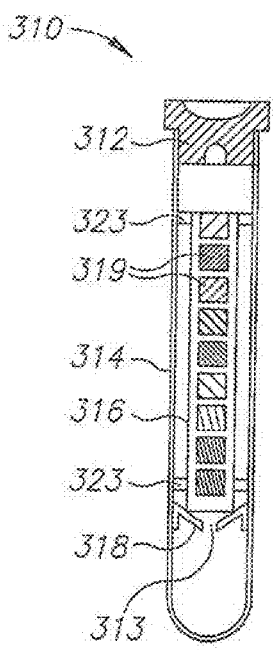
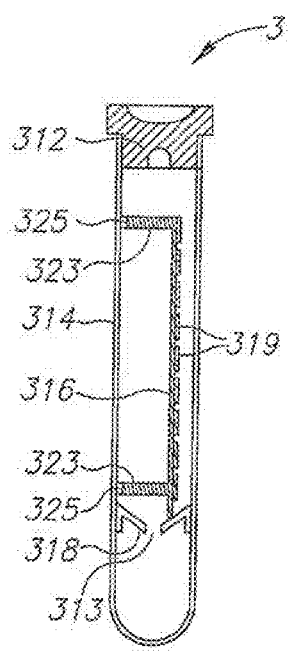
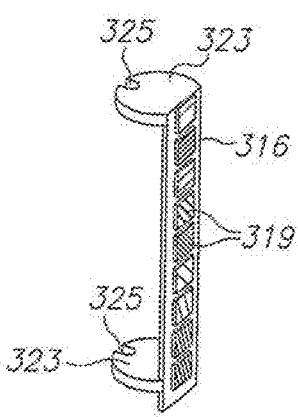
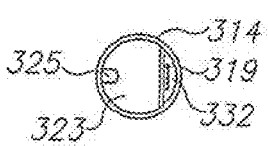
FIG.12E    FIG.12F    FIG.12G
FIG.12H

LIQUID TESTING ASSEMBLY

CROSS REFERENCE TO RELATED APPLICATION

The present application claims priority rights from U.S. Provisional Application 60/881,846 filed Jan. 23, 2007 and U.S. Provisional Application 60/960,634 filed Oct. 9, 2007.

FIELD OF THE INVENTION

The present invention relates to a liquid testing assembly for use in identifying constituents of liquids.

BACKGROUND OF THE INVENTION

Culturing microorganisms found in bodily fluids, including urine, to determine an illness is known in the art. Originally, such culturing was carried out in laboratories by collecting urine from a patient in a collection container, dipping a transfer utensil into the urine in the cup, streaking a culture medium in a Petri dish with the dipped transfer utensil, and then incubating the dish for a predetermined amount of time. After incubation, microbial colonies appeared on the medium and qualitative and quantitative results were determined.

Currently, dipslides are used for culturing urine samples in laboratory and non-laboratory settings, the latter including doctors' offices or medical clinics. Dipslides are culture (growth) medium coated, generally paddle-like, supports which are dipped directly into the urine collected in a collection container. Typically the paddle is coated with a different culture medium on each of its two sides; it comes with a container and stopper into which it fits during incubation after it has been dipped into the urine. The dipslides are typically incubated at the sample collection site, typically at about body temperature 37° C. Culturing generally requires that the stopper not be tightly sealed so that air can enter allowing for the growth of aerobic microorganisms. After initial incubation at the sample collection site, the dipslides are sent to a clinical laboratory for further incubation. If the results of culturing are negative, nothing further is done. If the results are positive, the dipslide is touched by a transfer utensil which in turn is used to streak agar in a Petri dish. The dish is then incubated at the laboratory, and, after a sufficient incubation period, examined to verify the previous positive results.

Dipslides are produced by many producers such as Oxoid Ltd., Basingstoke UK and Accepta Ltd., Manchester, UK. Several variants of dipslides are available, such as the Diaslide™ and Dipstreak™ produced by NovaMed Ltd. of Jerusalem Israel. These operate essentially in the same way as the simpler dipslides but with slight variations. In all cases, a urine collection container containing urine must be opened and the culture (growth) medium coated paddle must be dipped directly into the open container. After withdrawing the paddle, it is placed in a test tube and incubation is begun on-site. The whole process is performed by personnel not necessarily trained in handling potentially bio-hazardous materials, such as may be present in the urine.

Urinalysis today is done in a manner very similar to microbial culturing of urine discussed above. Urine is collected from the patient in a sample collection vessel. A test strip impregnated or coated with one or more reagents that react with one or more components often found in urine is dipped into the collection vessel. Changes in the reagent coated strip are then noted either visually or instrumentally. Typical urine test strips for use in urinalysis are manufactured by Roche Diagnostics, Basel, Switzerland, Bayer Corporation, Tarrytown, N.Y., (Multistix®) and Dialab GmbH, Vienna, Austria. Typical instrumental analyzers for reading dipped urine test strips are manufactured, for example, by Greiner Bio-One GmbH, Kremsmunster, Austria and Roche Diagnostics, Basel, Switzerland.

The problems with this type of urinalysis are similar to those encountered when culturing uropathogens as described above. A collection cup containing a potentially bio-hazardous liquid, urine, must be opened and a urine test strip must be dipped by a member of the medical staff or a laboratory technician into the liquid. In the case of urinalysis, instruments used for reading the urine test strip must be cleaned often since there is direct contact between the dipped test strip and the electronic reader and other parts of the instrument. When visually reading a urine test strip, the strip is compared to a chart provided by the manufacturer typically positioned on the bottle in which the strips are sold. Often, when comparing the color of the strips to the colors on the chart, the strip is brought near to the chart actually touching it. This allows for the spread of pathogenic organisms.

In view of the above, it would be advantageous to develop a closed system for microbial culturing and/or analysis of bodily fluids which reduces the dangers of contamination. Additionally, it would be advantageous to develop a closed system, which persons not necessarily trained in microbiological procedures could use without increasing the attendant health risks to them. There is also a need for a product that would allow dipslides to be sent for further testing in laboratory settings without escape of the liquid from the container and without it rewetting the medium coated paddle. It would also be advantageous to develop a system that is disposable and low cost.

SUMMARY OF THE PRESENT INVENTION

It is an object of the present invention to provide a liquid test assembly which reduces sample contamination while also reducing potential health hazards to health care workers.

It is an object of the present invention to provide a liquid testing assembly which does not expose a urine sample to the ambient when the sample is transferred from a collection container to a urine test strip assembly used for urinalysis or to a microbial culturing liquid testing assembly (dipslide) used for uropathogen culturing.

It is a further object of the present invention to provide a low cost liquid testing assembly for use in microbial culturing which requires less attention and training on the part of the personnel carrying out the culturing procedures.

It is a further object of the invention to provide an assembly for liquid testing usable at the site of sample collection and not necessarily in a laboratory setting.

It is yet another object of the present invention to provide a liquid testing assembly kit which includes a liquid testing assembly together with a sample collection container and a means for transferring the sample liquid from the collection container to the test vessel of the liquid testing assembly.

It is a further object of the present invention to provide a liquid testing assembly wherein the results of testing can be measured by an instrumental reader without removing the identifying material coated support of the assembly from its test vessel.

While what is discussed herein is described in terms of microbial culturing or chemical identification of urine samples, the liquid testing assemblies taught herein can be used for testing constituents of other bodily fluids or even liquids in other environments. If appropriately modified with the proper identifying materials, the assemblies can be used to identify constituents of other bodily fluids, such as blood or saliva. These constituents inter cilia may include drugs, alcohol, and pregnancy markers. Similarly, the identifying materials can be modified to be used in industrial environments, such as food processing or waste management. Also similarly, the assemblies of the present invention may be used for testing biological fluids of species other than humans.

In one aspect of the present invention there is provided a liquid testing assembly for testing a liquid. The assembly comprises a test vessel having a free end and a closed end and a stopper having first and second ends and adapted to fit into a free end of the test vessel. The first end faces into the interior of the test vessel, and substantially hermetically seals the interior of the test vessel from the ambient. The assembly also includes a support coated with one or more identifying materials for identifying one or more constituents of the liquid. The support is fixed to one or more of the stopper and the test vessel and extends into the interior of the test vessel by a predetermined distance when the stopper is positioned in the free end of the vessel. The liquid testing assembly when assembled is pre-evacuated to a predetermined vacuum sufficient to draw a predetermined volume of a liquid to be sampled into the test vessel from a liquid collection container. The predetermined volume is of such an amount that it wets the one or more identifying materials to ensure identification of one or more predetermined constituents present in the liquid.

In one embodiment of the assembly of the present invention, the liquid testing assembly also includes one or more liquid traps positioned proximate to the closed end of the test vessel and distal from its free end. The liquid trap is configured, sized and operative to prevent the liquid from flowing in the direction of the stopper.

In another embodiment of the assembly of the present invention, the one or more identifying materials is one or more culture media for culturing and determining the presence and nature of microbes present in the liquid. In some embodiments, the pre-evacuated test vessel includes a preselected gas composition artificially introduced into the test vessel to control the rate of microbial growth. In some embodiments, the trap is positioned at a distance from the stopper greater than the distance that the culture media coated support extends into the interior of the test vessel when the stopper is positioned in the free end of the test vessel.

In a further embodiment of the assembly of the present invention, the one or more traps are at least two traps. In some cases, the two or more traps are each a different type of trap.

In embodiments using traps, the traps are selected from one or more of the group of traps consisting of: conical plastic traps, floating plastic traps, liquid absorbing traps, and hydrogel traps. In some cases, the liquid absorbing traps are formed of hydrophilic sponge foam.

In a further embodiment of the assembly of the present invention, one of the one or more traps is a slow release trap and is positioned proximate to the free end of the test vessel and distal from the closed end of the test vessel. Liquid drawn from the liquid collection container forms a reservoir on a side of the slow release trap proximal to the stopper, the liquid slowly percolating from the reservoir through the slow release trap onto the assembly's support.

In another embodiment of the assembly of the present invention, the test vessel is a test tube and the stopper is a tube stopper.

In a further embodiment of the present invention, the one or more identifying materials are one or more chemical reagents for determining the presence of a chemical constituent of the liquid. In some embodiments, the identifying material is a plurality of chemical reagents positioned on a urine test strip.

In a further embodiment of the assembly of the present invention, the test vessel includes a bar code identification label which contains patient identifying information.

In yet another embodiment of the assembly of the present invention, the assembly further includes a means for distributing the drawn liquid. The means aids in the distribution of the drawn liquid as it passes over the identifying material coated support.

In another embodiment of the assembly of the present invention, the support is affixed in the stopper so that it is eccentrically positioned at its point of attachment with relation to the center of the stopper. The support therefore does not interfere with the insertion of a cannula which transfers liquid from the collection container to the test vessel.

In other embodiments of the assembly of the present invention, the test vessel further includes a permanently affixed identification tag.

In still another embodiment of the assembly of the present invention, the one or more identifying materials are culture media and the support has a first side and a second side. The support is formed to include a divider having an aperture therein and further constructed so that the liquid flushes only the first side of the support. The assembly further includes: 1. one or more liquid traps which are fixedly attached to a side of the divider proximate to the one or more culture media; 2. one or more liquid traps positioned proximate to the closed end of the test vessel and distal from the free end, the one or more liquid traps configured, sized and operative to receive liquid and prevent the liquid from flowing in the direction of the stopper; and 3. one or more inoculating elements which after they are in contact with, and wetted by, the one or more liquid traps attached to the divider are operative to inoculate the one or more culture media coating the second side of the support. In some versions of this embodiment, the side of the support that includes the culture medium that is inoculated contains a track on which the one or more inoculating elements travel when inoculation is effected. In other versions of this embodiment, the support is coated with one or more culture media only on the second side of the support. In such cases, the side of the support that lacks a culture medium is constructed as a channel to bring the liquid to the one or more traps positioned proximate to the closed end of the test vessel.

In another aspect of the present invention there is provided a disposable liquid testing kit. The kit comprises a liquid testing assembly for testing a liquid. The assembly comprises a test vessel having a free end and a closed end and a stopper having first and second ends and adapted to fit into the free end of the test vessel such that the first end faces into the interior of the test vessel. The stopper substantially hermetically seals the interior of the test vessel from the ambient. The assembly also includes a support coated with one or more identifying materials for identifying one or more constituents of the liquid. The support is fixed to one or more of the stopper and the test vessel. The support extends into the interior of the test vessel by a predetermined distance when the stopper is positioned in the free end of the test vessel. The kit also includes a liquid collection container for collecting a liquid and a cannula having one or more sharpened ends for piercing the stopper and transferring liquid from the container to the test vessel of the assembly. The liquid testing assembly of the kit when assembled is sterilized and pre-evacuated to a predetermined vacuum sufficient to draw a predetermined volume of a liquid to be sampled into the test vessel from the liquid collection container via the cannula. The predetermined volume is of such an amount so that it wets the one or more identifying materials to ensure identification thereby of one or more predetermined constituents present in the liquid.

In yet another aspect of the present invention there is presented a liquid testing system. The system comprises a liquid testing assembly defined as above and a reader for measuring and analyzing the results of a test done on a liquid by the assembly. The reader reads and analyzes the test results by optical measurement of the identifying material coated support; while the support is positioned in the test vessel. The reader comprises one or more spectroscopic detectors and a bar code reader for detecting electromagnetic radiation. The reader further includes a test vessel holder where the holder is configured to receive one or more test vessels and the holder is positioned to allow the spectroscopic detector and bar code reader to measure electromagnetic radiation. The reader also includes a microprocessor in electronic communication with the one or more spectroscopic detectors and the bar code reader to analyze the detected radiation. The microprocessor is also in electronic communication with one or more output means operative to present the test results and patient identifying data.

In an embodiment of the liquid testing system of the present invention the output means is selected from one or more of the following group of output means: a display, a printer, a patient file and a communications network.

In another embodiment of the liquid testing system, the test vessel holder is configured to hold a plurality of test vessels when reading and analyzing test results. The test vessel holder is rotatable bringing each test vessel into position for reading and analyzing by the one or more spectroscopic detectors and the bar code reader.

In yet another embodiment of the liquid testing system, the reader is a digital reader.

Definitions and Terminology Usage

Proximal—The direction closest to the stopper of the test vessel, the vessel typically, but without being limiting, being a test tube.

Distal—The direction furthest from the stopper of the test vessel, the vessel typically, but without being limiting, being a test tube.

Top—The direction or end of the test vessel that is closest to its stopper.

Bottom—The direction or end of the test vessel that is furthest from the stopper.

Constituent of a liquid—As used herein, the term can refer either to a chemical constituent or to a microbial constituent or to both as the context of the discussion requires.

Culture media—Media, and not medium, will generally be used herein. Typically, there is a plurality of such growth substances coating the liquid testing assembly supports discussed. This, however, is not to be understood as precluding the use of a single microbial growth substance should the user desire to use a single such substance.

Liquid testing assembly—The present invention contemplates two closely related assemblies, a microbial culturing liquid testing assembly and a chemical analysis liquid testing assembly. The former is for qualitative and semi-quantitative detection of microbes in a liquid while the latter is for qualitative and semi-quantitative detection of chemical species in a liquid. When not specifically indicated, the term liquid testing assembly applies to both types of assemblies. In view of the fact that urine testing is usually being discussed, urine strip liquid testing assembly is often used instead of chemical analysis liquid testing assembly.

Identifying material—The term refers either to a reagent to react with a chemical in the liquid being tested or to a culture medium for growing microbes in the liquid being tested. Whether a chemical reagent(s) or growth medium (media) is being referred to will be obvious from the context of the discussions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in greater detail than is necessary for a fundamental understanding of the invention. The description taken with the drawings make apparent to those skilled in the art how the several forms of the invention may be embodied in practice.

In the drawings:

FIGS. 1A-1C are schematic side views of a liquid testing assembly constructed according to various embodiments of the present invention, the assembly shown herein including a collecting trap;

FIGS. 2A and 2B are schematic side views of the liquid testing assembly constructed according to a first embodiment of the present invention using a slow release trap and a top view of the slow release trap, respectively;

FIGS. 2C and 2D are schematic side views of the slow release trap constructed according to the embodiment of the present invention shown in FIGS. 2A and 2B;

FIGS. 11A-11E are schematic front and side views of a liquid testing assembly constructed according to an eleventh embodiment of the present invention;

FIG. 11F shows another version of the liquid testing assembly constructed according to the embodiment of the invention in FIGS. 11A-11E;

FIGS. 12A-12B are schematic front and side views, respectively, of an embodiment of a liquid testing assembly of the present invention wherein the identifying materials are contained on a urine test strip;

FIGS. 12C-12D are two additional schematic views of the urine test strip support used in the embodiment of FIGS. 12A and 12B;

FIGS. 12E-12F are schematic front and side views, respectively, of a second embodiment of a liquid testing assembly of the present invention wherein the identifying materials are contained on a urine test strip;

FIGS. 12G-12H are two additional schematic views of the urine test strip support used in the embodiment of FIGS. 12E and 12F;

Similar elements in the Figures are numbered with similar reference numerals.

DESCRIPTION OF PREFERRED EMBODIMENTS

Figure 1D:
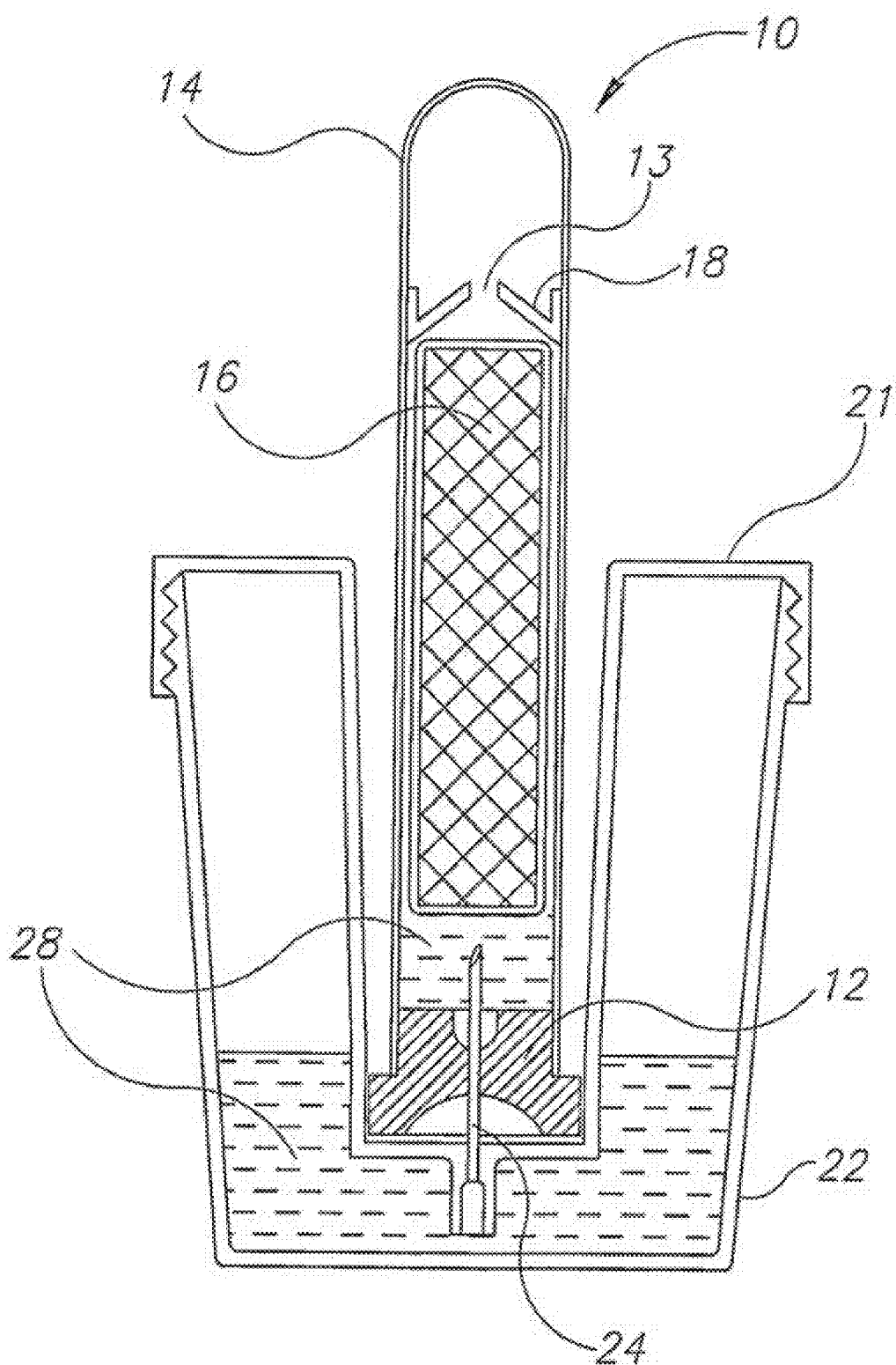
FIGS. 1D and 1E are schematic side views of the liquid testing assembly constructed according to the embodiments in FIGS. 1A-1C drawing off a liquid from a collection container.

The present invention provides a disposable closed sterile liquid testing assembly. Urine for testing is collected in a urine collection container and transferred to the liquid testing assembly for urine chemical testing or urine microbial culturing. The liquid testing assembly is comprised of a test vessel and a stopper/cap for substantially hermetically sealing the test vessel which has been pre-evacuated to a pre-selected vacuum. A support coated with one or more identifying materials is affixed to either the stopper/cap or the walls of the test vessel or both. The transfer of the liquid is effected by the vacuum of the pre-evacuated test vessel without directly exposing the liquid to the ambient.

Transfer is effected in a single step by using a needle cannula which pierces the stopper of the evacuated test vessel, typically an evacuated test tube, drawing a pre-selected volume of liquid from a urine collection container to the test vessel. Opening the closed collection container or liquid testing assembly is not required. Exposure to the ambient is obviated because the evacuated test vessel has fixed within it a urine strip or a culture (growth) media coated support, the latter also sometimes referred to herein as a dipslide.

The transfer procedure described above obviates the need for opening the urine collection container. Additionally, it does not require medical personnel to dip a urine test strip or a culture media coated support directly into a urine sample. As a result, the exposure of health care personnel untrained in stringent microbiological procedures to possible bio-hazardous materials is reduced. The transfer procedure also reduces the chance of sample contamination providing false positive readings.

The liquid testing assembly may also include one or more traps or other elements for preventing spillage of the liquid when the assemblies are handled or shipped. Furthermore, the one or more traps prevent rewetting of the dipslide or urine test strips after incubation has begun, regardless of the position of the liquid test assembly.

The liquid testing assembly may also include means for distributing the vacuum drawn urine over the culture (growth) medium or over the urine test strip. These means include slow release traps.

It is contemplated that the liquid testing assemblies of the present invention can be used for preliminary urinalysis or uropathogen culturing which can be carried out in a doctor's office or medical center. Initial microbial incubation at the site of urine collection is effected at 35-37° C. and then the culture is sent to a clinical laboratory for further incubation. The results can be determined visually or instrumentally at the laboratory. If the results of the microbial culturing are negative, the test tube is discarded. If the results are positive the stopper/cap of the liquid testing assembly is opened and a transfer tool, typically an inoculation loop, gathers material from the culture media coated support for streaking agar in a Petri dish. The dish is incubated and the results are again determined. Similarly, a positive result for the on-site urinalysis often requires that the urine sample in the urine collection container, or the urine sample in the liquid testing assembly, be sent to a laboratory for further analysis.

As noted above, the stoppered test tube is prepared so that it is under a predetermined vacuum. The vulnerability of the liquid testing assembly to contamination is reduced since the test tube is opened only immediately before gathering a sample for streaking of an agar filled Petri dish with a transfer utensil, such as an inoculation loop.

The present invention also teaches a kit including the above described liquid testing assembly, a urine collection container and a cannula for transferring a liquid from the collection container to the liquid testing assembly. The pre-determined, pre-calibrated vacuum in the substantially hermetically sealed test vessel allows for drawing off of a liquid sample from the sample collection container. The amount drawn off is approximately the smallest amount of sample required to sufficiently wet the culture media, or in the case of urinalysis, wet the reagent components coated, impregnated, or embedded in or on a urine strip.

While what is described herein is described with regard to bacteriological or other microbial culturing of urine samples, typically carried out to diagnosis urinary tract infections (UTIs), it should be evident to one skilled in the art that the assembly and kit of the present invention may be used with other bodily fluids such as blood and saliva. Constituents such as drugs and alcohol, in addition to bacteria or other microbes, can be detected in these bodily fluids. It should also be understood that the assembly of the present invention may be used with liquids other than bodily liquids. Wherever the culturing of microorganisms is required, such as with liquid food stuffs, water supply systems or liquid waste deposits, the assembly of the present invention may be used.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

It is to be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Reference is now made to FIGS. 1A-1C which show schematic side views of a liquid testing assembly 10 which includes a urine culturing test tube 14 constructed according to any one of several embodiments of the present invention. In all of the Figures, test tube 14 is pre-evacuated to a pre-selected pressure. Test tube 14 may be made of any of many transparent plastics known in the art, such as polystyrene (PS) or polyethylene terephtalate (PET), or even of glass.

Test tube 14 is covered by a stopper fitted to contain the vacuum for a pre-determined period, typically a period in excess of the shelf life of the culture media discussed below. Tube stopper 12 can typically be made of an elastomer such as moldable rubber, a soft polymeric resin, silicone or any other material that is flexible, liquid impermeable, and pierceable by a needle. The material should preferably be a material that may be self-sealing to liquids after being pierced. The exact shape of the stopper is easily producible by any of many techniques known in the art, such as, but without intending to be limiting, by injection molding. Vacutainers® manufactured by Becton Dickinson & Co. of Franklin Lakes, N.J. may be used as a source of test tubes 14.

Test tube 14 contains a support 16 typically coated on both sides with a culture medium. Typically, the medium on each of the sides is a different medium. In some embodiments, the medium on each side of support 16 is the same. In other embodiments, the support may have more than two sides, often four sides, each covered with a different culture medium to encourage growth of different microorganisms. In yet other embodiments, each face of support 16 may be coated with more than one medium and the various media on the individual faces are separated by dividers. Many different culture media are known in the art and are commercially available. Therefore, these media will not be discussed herein.

Liquid testing assembly 10, here a microbial culturing assembly, also contains a trap 18 shown here as a conical trap, typically made of plastic. Trap 18 contains a small aperture, typically of the order of 2-3 mm in diameter, and is intended to trap excess liquid and prevent return of the trapped liquid to culture media coated support 16. This is true regardless of the position of the test tube. Test tube 14 need only be standing vertically when the urine sample is dripping onto and percolating down culture media coated support 16. After wetting the media, test tube 14 can be held in any position, for example horizontal, vertical or diagonal, because of trap 18.

FIGS. 1A and 1B show two views of the same microbial culturing liquid test assembly 10 in which the culture media coatings on the two sides of the media support 16 are parallel to each other. FIG. 1C shows a schematic side view of an embodiment of microbial culturing liquid test assembly 10 where the two faces of support 16 coated with culture media are not parallel to each other. In FIGS. 1A-1C (and FIGS. 1D-1E discussed below) the connection of media support 16 to test tube 14 or stopper/cap 12 is not shown as these can be any of many different types. These connections, however, will be shown in all of the following Figures. There, it will become apparent that culture media coated support 16 may be supported and connected directly to stopper/cap 12 in any manner known to those skilled in the art. Alternatively, or additionally, support 16 may be attached to and/or supported by the walls of test tube 14.

Figure 1E:
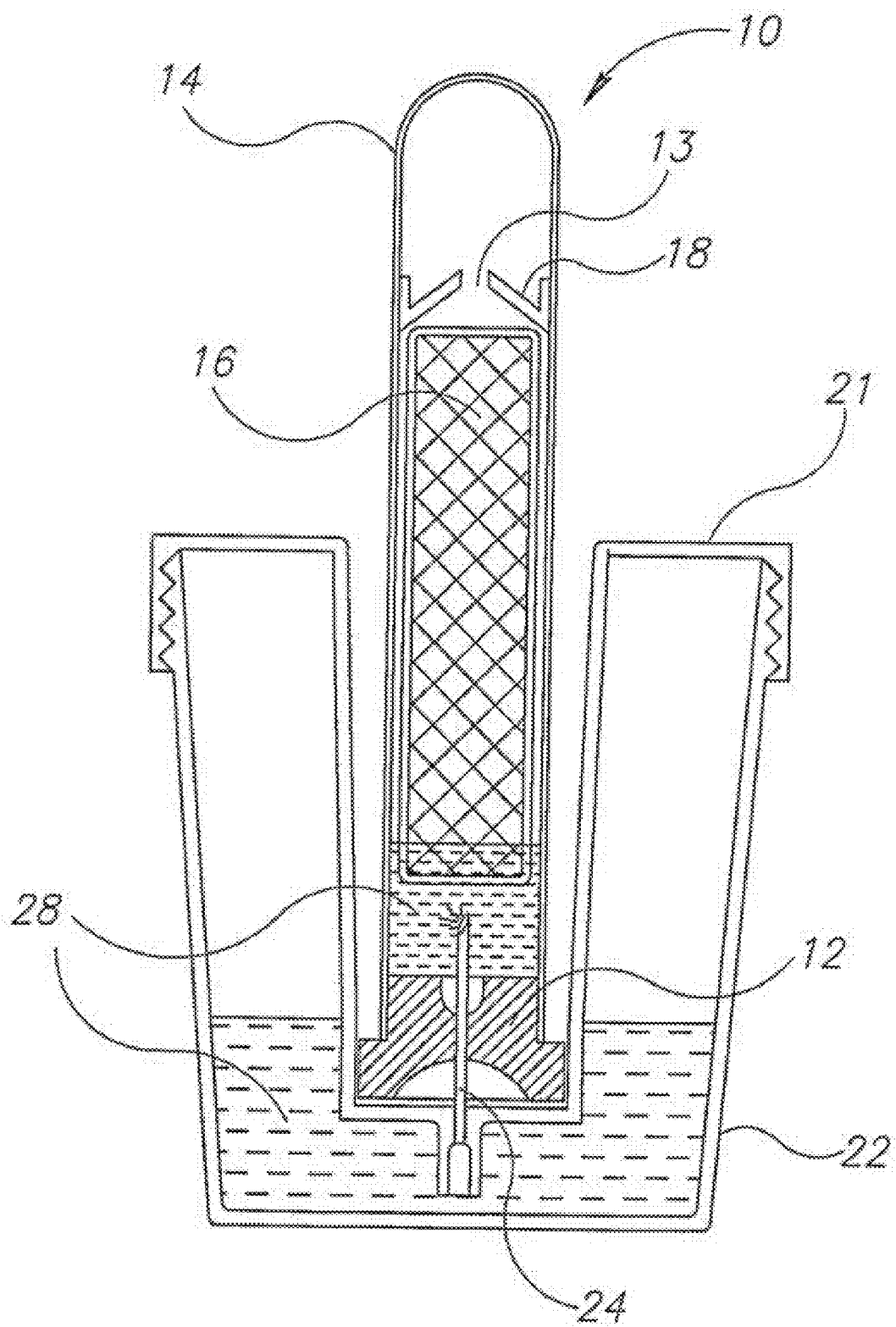

FIGS. 1D and 1E show the transfer of urine or other liquid from collection container 22 to microbial culturing liquid assembly 10. The only difference between FIG. 1D and FIG. 1E is that the vacuum in the test tube of FIG. 1D allows for entry of a volume of urine only up to culture medium support 16 while in FIG. 1E the vacuum allows for entry of a volume of urine that reaches and covers part of culture medium support 16. Cannula 24 is actually attached to, and part of, closed urine collection container 22 having top 21. Cannula 24 can be used to pierce stopper 12 and transfer a predetermined volume of sample from collection container 22 to partially evacuated test tube 14. Collection containers with cannula are known in the art and sold commercially, for example, by Becton Dickinson and Co. of Franklin Lakes, N.J.

Test tube 14 with stopper 12 and with culture media coated support 16 attached therein is prepared so as to be under a pre-determined vacuum. The pre-determined vacuum is empirically determined and is intended to draw off a pre-determined volume of sample from urine sample collection container 22 through cannula 24.

The predetermined vacuum obviates the need for the technician to open the urine collection container 22 and to dip the identifying material coated support 16 into collected urine 28.

It is expected that a vacuum of 1-3 inches of Hg (approximately 25-76 Torr or about 0.033-0.100 bar) in a 10 ml tube will be sufficient to draw about 1 ml of sample into the pre-evacuated test tube 14 which forms part of liquid testing assembly 10. This is expected to be sufficient to wet culture media coated support 16.

Becton-Dickenson's 10 ml Vacutainers® are typically produced so as to have a vacuum of about 18-20 inches Hg (about 500 Torr or about 0.66 bar) when about 9 ml of urine is to be drawn from a urine collection cup into a 10 ml test tube. Such volumes are far in excess of what is required for microbial culturing of urine samples with the liquid testing assemblies of the present invention. In the present cases, typically, approximately 0.7-1.5 ml of urine is required. This can be obtained with a vacuum of 2-5 inches of Hg, a vacuum the magnitude of which still leaves a significant amount of air in the test tube.

Liquid testing assembly 10 (FIGS. 1A-1C), with their pre-calibrated vacuums, draw off sample liquid in a manner similar to that shown and discussed in U.S. Pat. No. 6,921,395 to Carano et al; U.S. Pat. No. 4,927,605 to Dorn et al; U.S. Pat. No. 4,116,066 to Mehl et al; and U.S. Pat. No. 4,300,404 to Mehl et al, all herein incorporated by reference in their entireties. In these patents, an evacuated test tube is mated with a sample collection vessel. Sample liquid moves under vacuum from the collection vessel to the test tube via a needle cannula which pierces a stopper of the test tube. The covered sample collection container typically possesses a recess in its cover which contains the cannula used in the liquid transfer. The recess functions as a female structure to receive the evacuated test tube, the male structure, during sample transfer.

In some embodiments, the pre-vacuum includes other gases that are artificially introduced to accelerate or decelerate microbial growth on culture media coated support 16. These gases could be oxygen, nitrogen, etc. as the case dictates. This results in a gas mixture with component percentages different from ambient atmospheric percentages.

It should be noted that when microbial culturing is being effected using the liquid testing assemblies of the present invention, the stopper or cap must be partially opened. This enables aerobic or aerophilic microbes to be cultured.

It should be noted that the liquid testing assemblies of the present invention allow for gentle shaking of the assemblies to ensure full wetting of the growth medium by the liquid.

Because culture media coated support 16 is not exposed to the air until, and if, the initial testing is positive, air borne microorganisms only minimally, if at all, contaminate the specimens. If the test is positive, as noted above, a transfer utensil, typically an inoculation loop, is used to gather material from support 16 to streak a culture medium filled Petri dish. The dish is then incubated entirely in a clinical laboratory. Additionally, because the fluid is pulled off by vacuum directly from a closed sample collection vessel to a closed test tube, the risk of infection to the health care personnel is reduced.

In FIG. 2A, to which reference is now made, there is presented another embodiment of the present invention. Since the embodiment is similar in structure and operation to the microbial culturing liquid testing assembly 10 shown in the embodiments of FIGS. 1A-1E, only novel features of the structure in FIG. 2A will be discussed. Connectors 15 join culture media coated support 16 to stopper (or cap) 12 by being fixed or implanted in the latter. Alternatively, culture media coated support 16 could be connected to the side walls of test tube 14. There is a slow release trap 30 positioned near stopper (or cap) 12.

Reference is now made to FIG. 2B where a top schematic view of a slow release trap is shown. Trap 30 contains slots 32 which allow for slow entry of urine transferred from a collection container as shown in FIGS. 1D and 1E into the body of test tube 14. Slow release trap 30 allows for better wetting of culture media coated support 16.

Figure 2E:
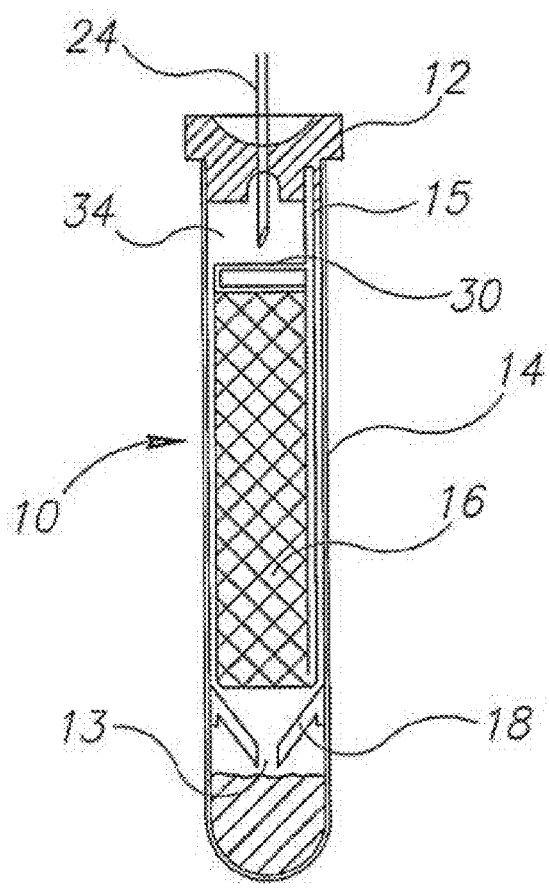
FIGS. 2E and 2F are two schematic views of the slow release trap constructed according to an embodiment of the present invention shown in FIGS. 2A and 2B.
Figure 2F:
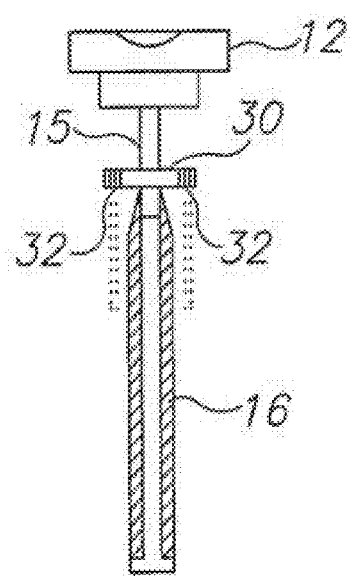

FIGS. 2C and 2D and FIGS. 2E and 2F show additional views of two versions of slow release trap 30 and its slots 32. Liquid held in reservoir 34 percolates through slots 32 over culture media coated support 16. Cannula 24 is shown in FIG. 2D and is similar to cannula 24 shown and discussed in conjunction with FIGS. 1D and 1E.

Figure 3:
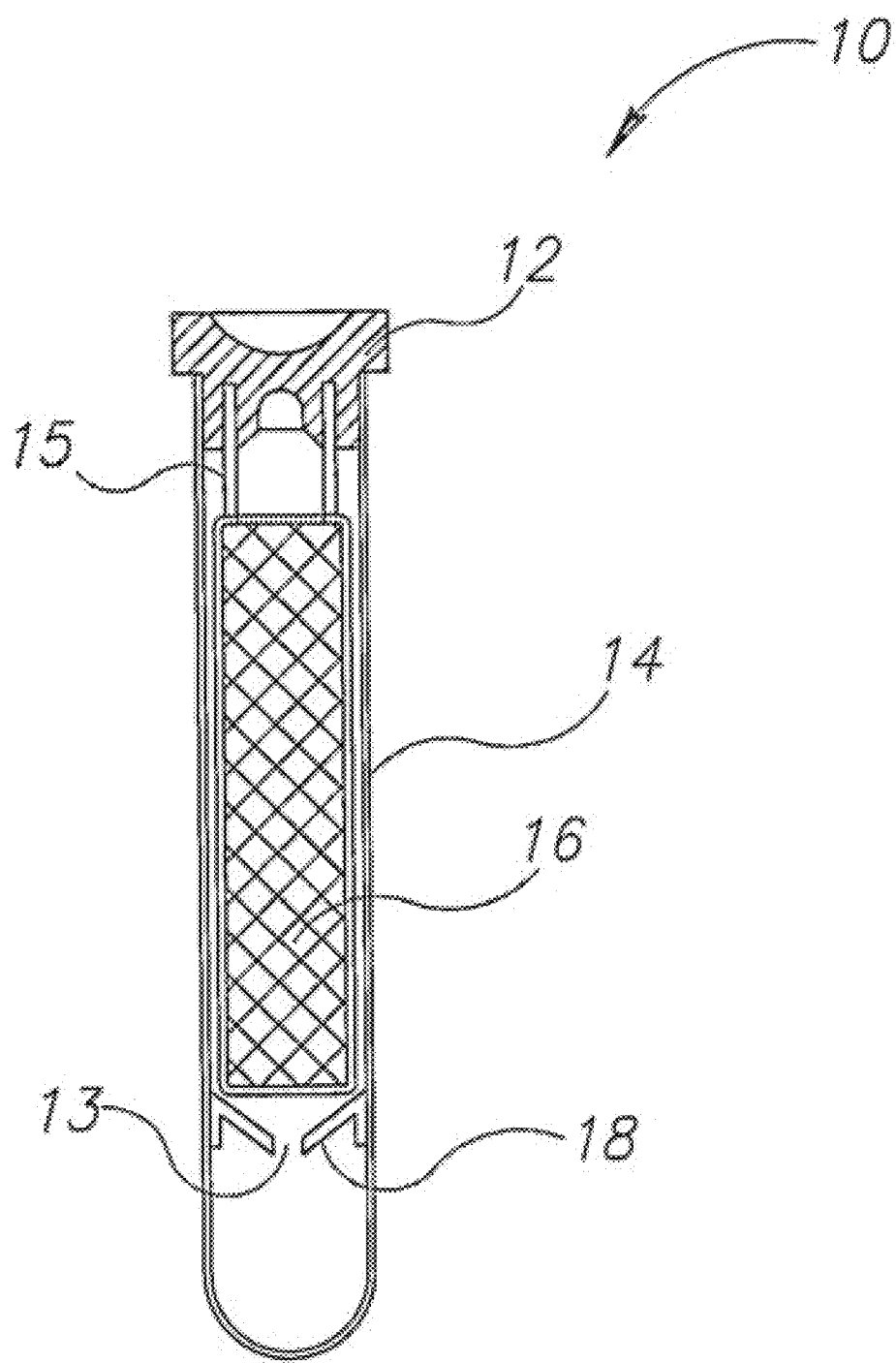
FIG. 3 is a schematic side view of a liquid testing assembly constructed according to a second embodiment of the present invention, an embodiment without using the slow release trap.

FIG. 3 is a view of the same embodiment as FIG. 2A but without the slow release trap 30.

Figure 4:
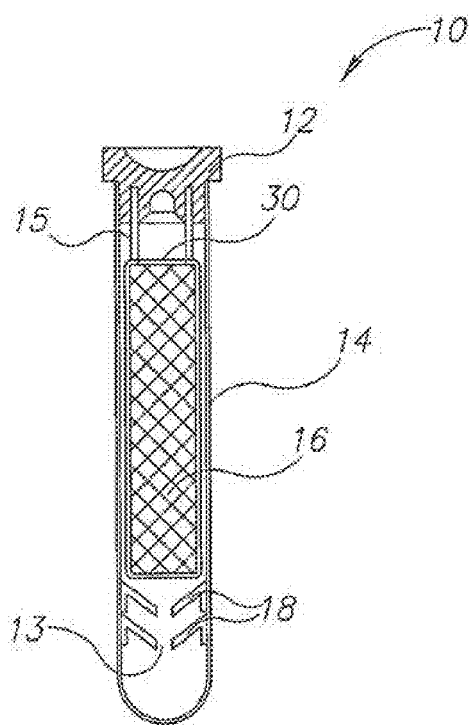
FIG. 4 is a schematic side view of a liquid testing assembly constructed according to a third embodiment of the present invention, the embodiment employing a double collecting trap.

FIG. 4, to which reference is now made, shows a third embodiment of the present invention, one very similar to the embodiment shown in FIG. 2A. Structural features which are the same as in previous Figures are labeled with the same numbers and are not discussed again. The novel feature in this third embodiment is the double lower conical trap 18. Both conical traps 18 are constructed and operative as discussed above in conjunction with FIGS. 1A-1C.

Figure 5:
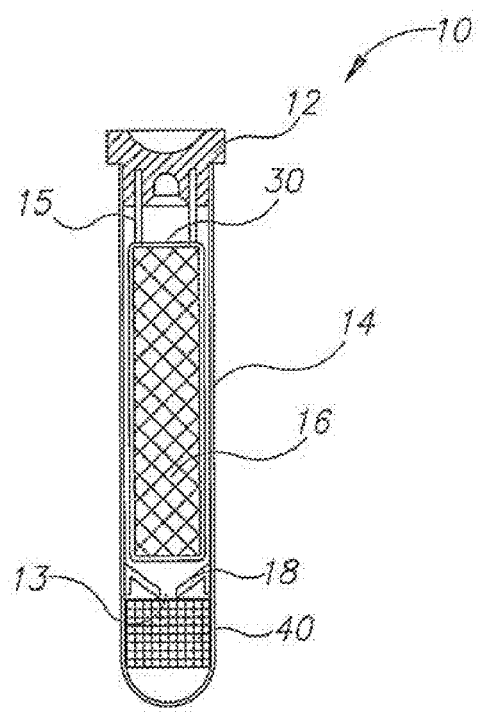
FIG. 5 is a schematic side view of a liquid testing assembly constructed according to a fourth embodiment of the present invention, the embodiment also including a hydrophilic foam trap.

Reference is now made to FIG. 5 where a fourth embodiment of the present invention is shown, one similar to the embodiment shown in FIG. 2A. The novel feature here is an expanding medical grade hydrophilic cellular foam 40 positioned at the bottom of test tube 14. The foam expands when absorbing liquids and prevents the flow of liquid toward the top of test tube 14. The foam acts as a second liquid trap at the bottom of test tube 14.

In yet another embodiment, a trap made from a hydro-gel material can be used instead of a foam trap.

Figure 6A:
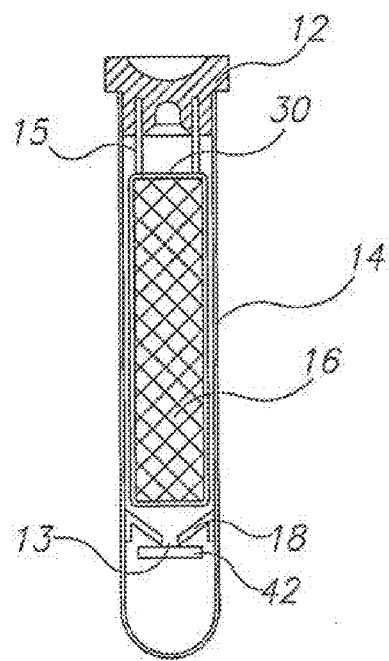
FIGS. 6A and 6B are schematic side views of a liquid testing assembly constructed according to fifth and sixth embodiments of the present invention.

In turning to FIG. 6A, a fifth embodiment of the present invention is shown. It is very similar to the one shown in FIG. 2A and is similarly numbered. The additional feature here is a floating disc 42, typically made from an elastomeric rubber, silicone or plastic material that serves as an additional trap at the bottom of test tube 14. It acts in conjunction with conical trap 18 to prevent the backward flow of urine by blocking the small aperture of conical trap 18.

Figure 6B:
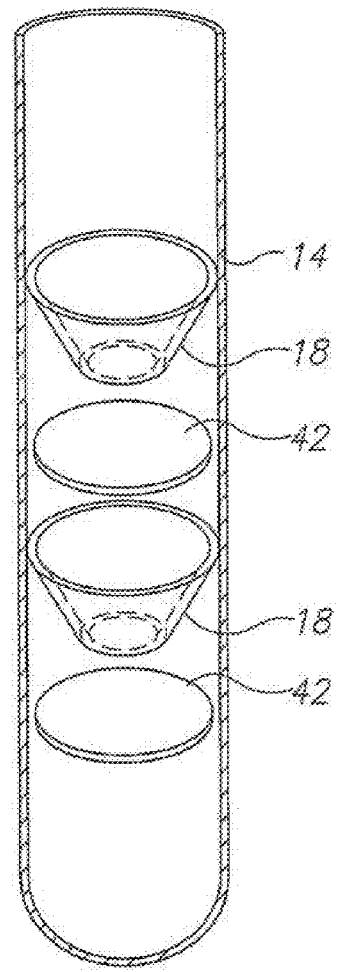

FIG. 6B shows a sixth embodiment of the present invention. There is a double conical trap 18, each conical trap 18 being covered by a floating disc trap 42. Typically, both the conical traps and the floating disc traps may be formed of light weight plastic. It can readily be understood by one skilled in the art that in some embodiments the two floating discs 42 by themselves can serve as the trap and the conical collection traps 18 need not be present.

Figure 7:
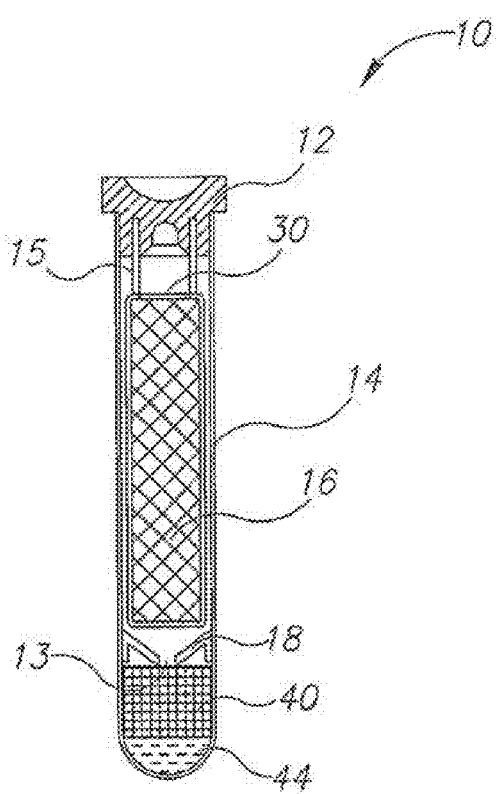
FIG. 7 is a schematic side view of a liquid testing assembly constructed according to a seventh embodiment of the present invention.

Reference is now made to FIG. 7 where another embodiment of microbial culturing liquid testing assembly 10 is shown. The assembly is similar in construction and operation to the embodiment shown in FIG. 5. The additional feature here is a hydrogel or solution reservoir 44 which contains material that "captures" liquid not absorbed by foam 40.

Figure 8A:
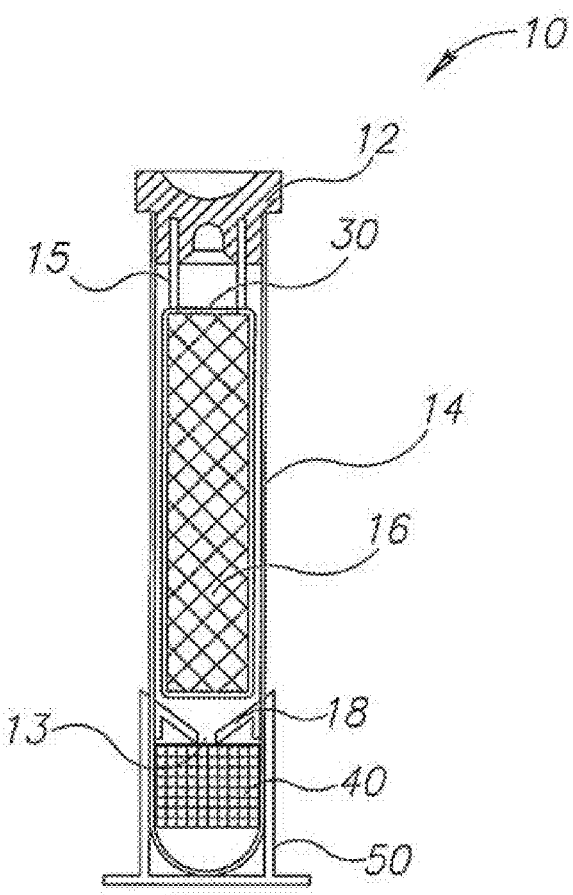
FIGS. 8A and 8B are schematic side views of a liquid testing assembly constructed according to an eighth embodiment of the present invention and a stand for its use, respectively.
Figure 8B:
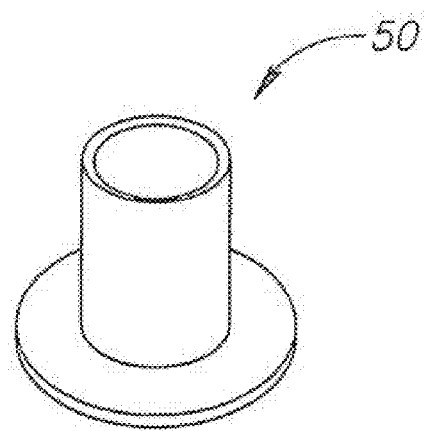

In turning to FIG. 8A, another embodiment of the invention very similar to the one shown in FIG. 5 is illustrated. The additional feature here is a stand element 50 affixed permanently to the bottom of microbial culturing liquid testing assembly 10 allowing for better stability on a level surface. Stand element 50 is shown separately in FIG. 8B. In other embodiments, stand element 50 may be a separate element into which test tube 14 may be inserted and then withdrawn as needed.

Figure 9A:
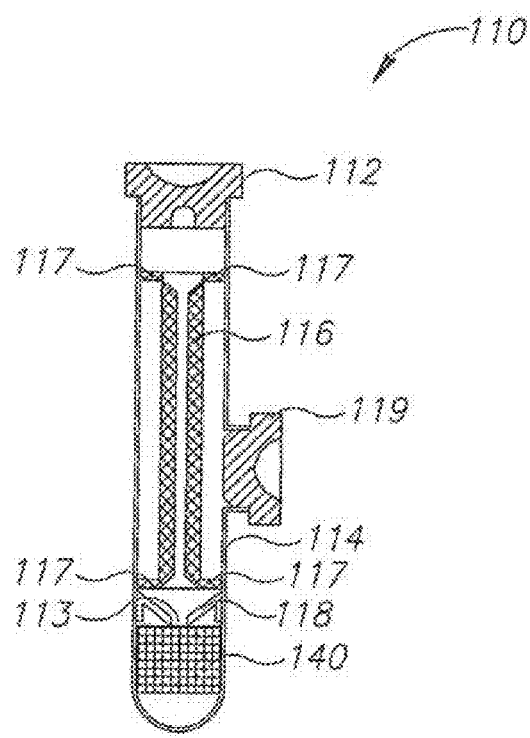
FIGS. 9A and 9B are schematic side views of a liquid testing assembly constructed according to a ninth embodiment of the present invention.
Figure 9B:
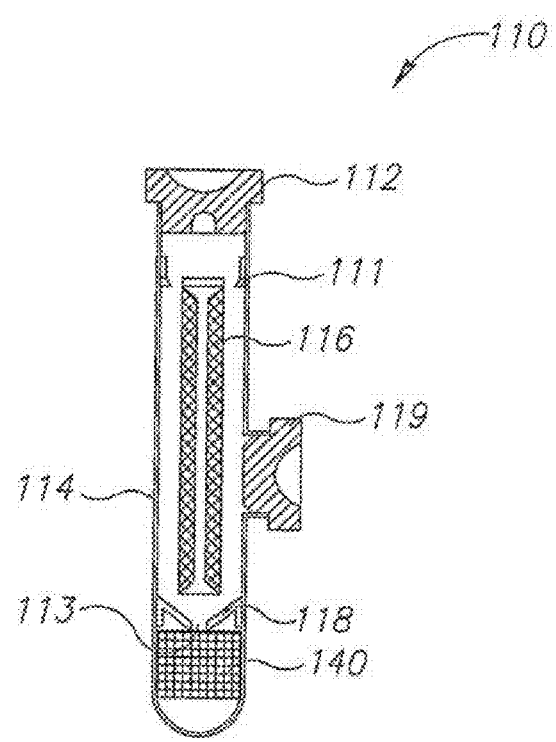

FIGS. 9A-9B show yet another embodiment of the present invention. FIGS. 9A-9B both show test tube 110 which is very similar to the test tubes of the embodiments shown in previous Figures, for example, in FIG. 5. Many of the elements shown in FIGS. 9A-9B have been discussed previously and will not be discussed again as their structure and operation is similar. These elements have been numbered as with similar elements in previous Figures but with the addition of an introductory digit "1".

The novel feature in this embodiment is a lateral opening and stopper 119. This lateral opening allows for inserting an inoculating instrument for touching the culture medium on support 116 and then removing the instrument for streaking on a culture medium in a Petri dish. The difference between FIGS. 9A and 9B is the point and method of attaching culture media coated support 116 within test tube 114. In both FIGS. 9A and 9B, urine slowly passes attachment elements 117 and 111, respectively, onto and along culture medium coated support 116. The liquid then moves through aperture 113 in conical trap 118 and is absorbed by hydrophilic foam 140.

Figures 10A, 10B:
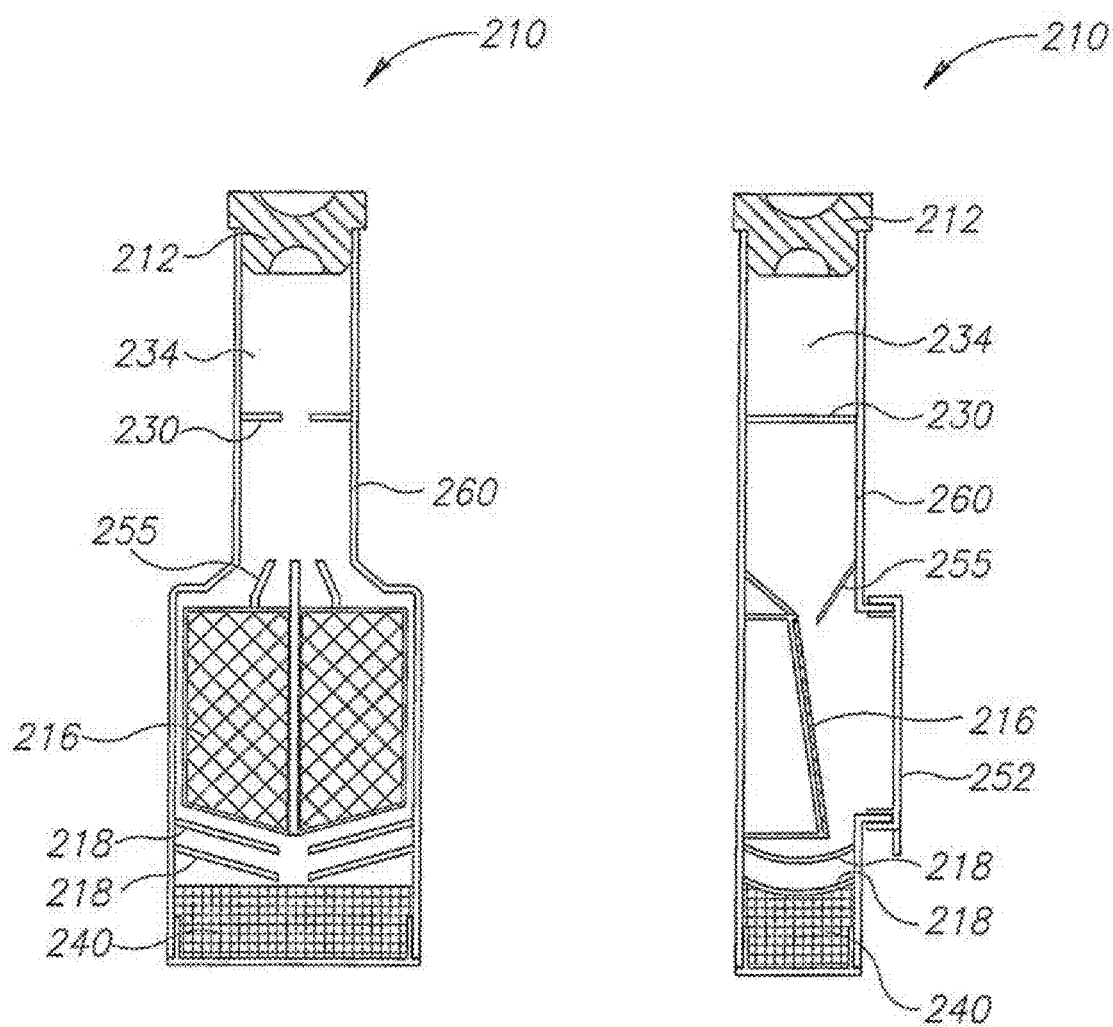
FIGS. 10A and 10B are schematic front and side views of liquid testing assemblies constructed according to a tenth embodiment of the present invention.

Reference is now made to FIGS. 10A and 10B which show front and side views, respectively, of yet another embodiment of the present invention. Many of the elements shown in FIGS. 10A-10B have been discussed previously and will not be discussed again as their structure and operation is similar. These elements have been numbered as with similar elements in previous Figures but with the addition of an introductory digit "2". Microbial culturing liquid testing assembly 210 includes two conical traps 218 and a hydrophilic foam 240. Culture medium coated support 216 is sloped for better dispersal of the liquid over culture media coated support 216. There are also liquid dispersing elements 255 to assist in better dispersing the entering liquid over support 216. Microbial culturing liquid testing assembly 210 has a tightly fitting cover 252 on its side. The embodiment also includes a slow release trap 230 through which the urine passes slowly when leaving reservoir 234.

Figure 10D:
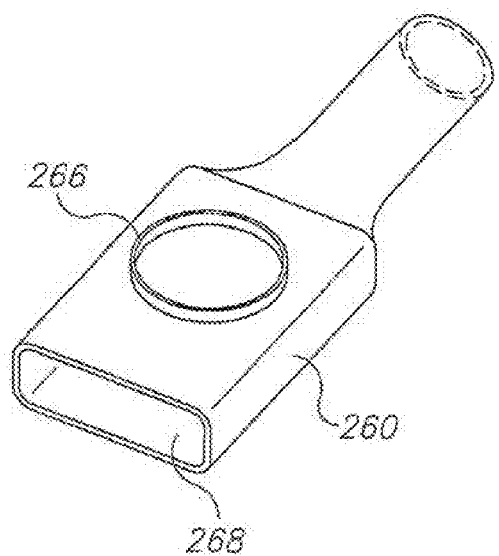
FIGS. 10C-10H are schematic views of elements in the liquid testing assemblies constructed according to the embodiment shown in FIGS. 10A-10B.
Figure 10G:
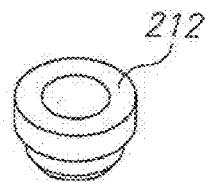
Figure 10F:
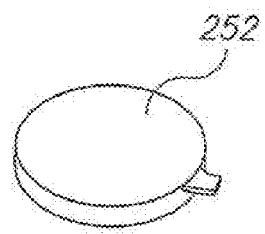
Figure 10E:
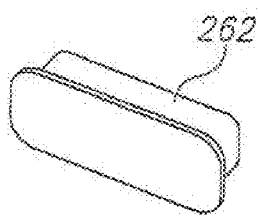
Figure 10H:
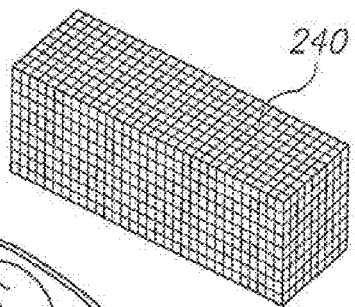

FIG. 10D shows the housing 260 of microbial culturing liquid testing assembly 210 shown in FIGS. 10A and 10B. Housing 260 has an opening 268 in its bottom (FIG. 10D) into which bottom cover 262 (FIG. 10E) fits tightly. Housing 260 also has a lateral opening 266 on which cover 252 (FIG. 10F) fits. FIG. 10H shows the foam positioned at the closed end of testing assembly 210.

Figure 10C:
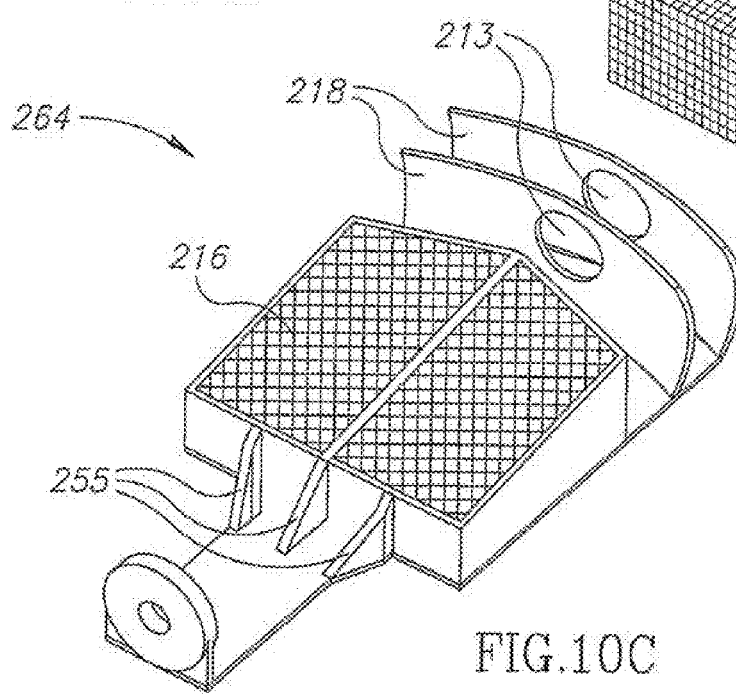

Insert 264, shown in FIG. 10C, is inserted through bottom opening 268 (FIG. 10D) of housing 260. FIG. 10C shows that insert 264 may be, but without intending to be limiting, of a unitary construction. Insert 264 includes dispersing elements 255 for better dispersing the liquid over culture media coated support 216. Insert 264 also includes double conical traps 218 including small apertures 213.

As noted above, the stopper (or cap) 212 of microbial culturing liquid testing assembly 210 must be kept partially open during incubation to allow culturing of the microbes. As a result, volatile substances can escape. In some embodiments, therefore, there is added at the bottom of the liquid testing assembly one or more materials that prevent the escape of volatile gases outside the test tube of the assembly when the test tube is opened.

Reference is now made to FIGS. 11A-11E where front and side views of another embodiment of a microbial culturing liquid testing assembly of the present invention is shown. This embodiment is similar to the ones shown in FIGS. 5 and 2A. Many of the elements shown in FIGS. 11A-11E have been discussed previously and will not be discussed again as their structure and operation is similar. These elements have been numbered as with similar elements in previous Figures but with the addition of an introductory digit "5".

Tube stopper 512, constructed as described in conjunction with FIGS. 1A-1C, essentially hermetically seals test tube 514. A culture medium support 516 is coated with one agar culturing medium 590 on its first side and with a second agar culturing medium 592 on its second side. It should be understood that in some instances, media 590 and 592 may be identical.

Support 516 is fixedly attached to tube stopper 512. Support 516 is constructed and positioned so that when the liquid to be tested, typically, but without being limiting, urine, enters test tube 514, the liquid descends to the bottom of test tube 514 via flushing channel 596 and not through inoculating channel 598 as discussed below. An arrow in FIGS. 11A and 11E indicates the direction of liquid flow.

In all of FIGS. 11A-11E (and FIG. 11F), support 516 is formed to include a divider 582 which prevents liquid from directly entering inoculating channel 598. Divider 582 includes an aperture 583 which facilitates the wetting of a hydrophilic cellular foam 541 by liquid which becomes trapped therein, as discussed further below, during the liquid transfer step best seen in FIG. 11B. Foam 541 is attached to the side of divider 582 proximate to the agar coatings. While divider 582 is generally positioned transverse to the long axis of test tube 514, divider 582, in some instances, may be slightly sloped toward flushing channel 596.

An expanding medical grade hydrophilic cellular foam 540 is positioned at the bottom of test tube 514. The foam expands when absorbing liquids and prevents the flow of liquid in the direction of stopper 512 should test tube 514 become inadvertently inverted. Foam 540 acts as a liquid trap at the bottom of test tube 514.

The liquid testing assembly of this embodiment also contains an inoculating element 594, typically, but without being limiting, a bead-like element, that is in contact with foam 540 when test tube 514 is in its orientation as shown in FIGS. 11A and 11C-11E (and FIG. 11F).

Inoculating element 594 may have many different shapes, for example spherical, cylindrical, and ellipsoidal. These shapes are exemplary only and are not intended to be limiting. Element 594 may be made from glass, substantially inert polymeric materials, or metals. These materials are also not intended to be limiting.

In some variations of the embodiment in FIGS. 11A-11E, there may be more than a single inoculating element 594, that is, for example, more than a single bead or cylinder. Similarly, inoculating element 594 may be constructed so that it has finger-like projections with which to streak culturing medium 592.

Inoculating element 594 may move freely in the direction of stopper 512 as in FIGS. 11A-11E; alternatively, support element 516 may be constructed with a track (not shown) which guides inoculating element 594 as it moves towards stopper 512.

As can be seen in FIG. 11B, divider 582 and attached foam 541 act as a stop for inoculating element 594 when it moves in the direction of stopper 512.

While hydrophilic foam traps 540 and 541 have been shown in FIGS. 11A-11E (and FIG. 11F), other types of traps such as those described hereinabove may also be used.

Liquid may be brought to the liquid testing assembly using a collection container 522 and cannula 524 similar to the ones shown in FIG. 1D, for example, and described in conjunction therewith. FIG. 11B shows this transfer of liquid 599 through cannula 524; the collection cup is not shown in the Figure.

Inoculating element 594, typically a rollable bead-like element, rolls from the foam 540 end of test tube 514 towards the stopper 512 end of test tube 514 when the assembly is inverted as in FIG. 11B from its usual orientation as in FIG. 11A. It is wetted by foam 541, which has been wetted during the liquid transfer phase as shown in FIG. 11B, by some of the liquid 599 that has reached foam 541 via aperture 583. When closed test tube 514 is returned to its original orientation wetted inoculating element 594 moves toward, and then rests on, foam 540. During its return to foam 540, inoculating element 594 intermittently streaks culture medium 592 generally at distances more or less equal to the circumference of the bead. These streaks are indicated by crosses 588 in FIG. 11D.

The liquid 599 that has wetted foam 541 does not descend via inoculating channel 598 towards foam 540. When test tube 514 is inverted from its orientation in FIG. 11B back to its orientation shown in FIGS. 11A and 11C-11E (and FIG. 11F), liquid 599 enters flushing channel 596 and is absorbed by, and trapped in, foam 540.

Typically, but without being limiting, inoculating element 594 deposits less than about 25 microliters on agar culture medium 592 while medium 590 may typically be flushed by about 1-1.5 ml of fluid.

In yet other variations of the embodiment shown in FIGS. 11A-11E, and as shown in FIG. 11F, there may be only one agar medium present, agar medium 592 (not visible) required for streaking. The second side of support 516 may be devoid of any culture medium 590.

Flushing of the assembly in FIGS. 11A-11F allows for the growth of a large microbial culture and a quick positive/negative determination. If the results obtained in the doctor's office or the medical center are positive, a more precise culturing is repeated in a professional clinical laboratory.

When using the microbial culturing liquid testing assembly shown in FIGS. 11A-11F, the inoculation process may begin in the doctor's office or in a medical center. Typically, the direct flushing of medium 590 is done with about 1-1.5 ml of liquid and medium 592 is inoculated with about 25 microliters of liquid.

After a first period of incubation at 35-37° C. in the doctor's office or medical center, the microbial growth on medium 590 allows for a quick visual determination of whether the results are positive or negative. This can be done using commercially available colony density charts which show colony forming units per milliliter (CFU/ml). Typically, 70 to 80% of the samples are negative and there is no need to open the samples or send them on to a professional clinical laboratory for further testing.

If the results of the sample in the doctor's office or medical center are positive, the sealed testing assembly is sent to a professional microbiological laboratory for final incubation and more precise testing. More precise colony counts are made using instrumental methods based on measurements of color and colony density. At the professional laboratory, additional testing is also done on medium 592. This testing includes the steps of isolation, identification, detection and enumeration of microorganisms and pathogens.

The worker at the professional laboratory may open the liquid testing assembly, remove the support with its media coatings and test for sensitivity to antibiotics of one or several microorganisms and/or perform dilution studies on these microorganism(s). For these tests, the lab worker may remove a tiny sample of the microorganism(s) on the media coated support and grow them in a controlled manner in a Petri dish. The support may then be returned to the test tube which is then recapped.

In the following embodiments, a chemical analysis liquid testing assembly for testing chemical constituents of urine using urine test strips will be discussed. As with liquid testing assemblies employing culture media coated supports suitable for microbial culturing discussed above, the test tube used for urine strip liquid testing assemblies need not be opened during urine transfer and testing. Similarly, the cover of a urine collection container need not be opened. Urine can be transferred from the collection container to the test tube using the test tube's predetermined vacuum. As a result, health care personnel are spared exposure to possibly bio-hazardous urine constituents and the hazards of a wetted urine strip. As with the assembly containing a culture media coated support, the same collection container can be used to supply samples for additional urinalysis testing if the initial on-site reading of the wetted strip is positive.

In chemical analysis liquid testing assemblies, more specifically, urine test strip liquid testing assemblies, the support can be a support to which a paper urine test strip has been affixed. In other embodiments, the paper of the urine strip is deemed to be the support and the chemical reagent or reagents are coated on or impregnated in the paper. The urine strip or the separate support to which the strip is affixed can be attached in any of many ways known in the art. Attachment may be effected to the stopper or to the walls of the test tube or to both the stopper and walls of the liquid testing assembly. If attached and supported by the walls, the urine strip should be spaced apart from the walls.

Chemical analysis liquid testing assemblies can be designed to use the full range of traps described above in conjunction with microbial culturing liquid testing assemblies. These include slow release traps positioned proximal to the stopper of the assembly.

Typically, the urine strip is fixed to, or implanted in, the stopper or walls of the test vessel eccentrically so as not to interfere with the needle cannula when it pierces the stopper during the liquid transfer process. The strip should be spaced apart from the wall of the test tube so as not to be continuously wetted by the urine because of capillary action and to prevent air or liquid bubbles from becoming entrapped between the strip and the walls of the test tube. A support element can be affixed to the strip inside the test tube to keep the strip spaced apart from, and essentially parallel to, the wall of the test tube. In general, the liquid should wet the strip and then fall to the bottom of the test tube.

The volume of urine transferred to the test tube is governed by the pre-determined vacuum in the test tube. The volume of urine transferred via the needle cannula to the liquid testing assembly which contains the urine strip is less than the volume of the entire test tube. For a 10 cc test tube about 3 cc are drawn into the test tube. It is estimated that about three cc of liquid can be drawn off by a vacuum of about 4 inches of Hg. For a 3 cc test tube, about 0.7-1.2 cc of urine is needed.

The height of the liquid in the test tube should typically extend to just above the bottom of the urine strip.

As long as the urine strip is not immersed in liquid, the results of the urine test strip can be read visually while the strip remains in the test tube. The visual reading is typically compared against reagent color charts provided by the manufacturer of the strips. Visual readings can be made regardless of whether the test tube is in its vertical or its horizontal position.

Excess liquid accumulates at the bottom of the test tube when the test tube is held vertically during and after the urine has wet the urine test strip. After being out of the urine for 60 seconds, the test strip can be visually read. It should be noted that the urine test strip can also be read when the test tube is held horizontally. When the test tube is lying horizontally and a reading is to be made, the liquid should lie between the strip and the wall of the test tube without actually touching the strip.

In addition to visually reading the urine strip, the results of the test may be obtained by using an instrumental analyzer/reader. In both cases, the reading is made while the identifying material coated support is still inside the test vessel. Typically, the instrumental analyzer/reader, hereinafter "reader", analyzes the strip optically. The reader typically will contain a receiving inlet into which the entire test tube, except for the stopper, is inserted. The reader reads the results through the transparent walls of the test tube, along the entire length of the test tube.

FIGS. 12A and 12B, to which reference is now made, illustrate a urine strip liquid testing assembly constructed according to a first embodiment of the present invention. FIGS. 12A and 12B show front and side, respectively, schematic views of this first embodiment.

Liquid testing assembly 310 includes a test tube 314 pre-evacuated to a pre-selected pressure. Test tube 314 is typically made of any one of many transparent plastics known in the art, such as polystyrene (PS) and polyethylene terephtalate (PET), or even of glass. Vacutainers® manufactured by Becton Dickinson & Co. of Franklin Lakes, N.J. may be used as a source of test tubes 314.

Test tube 314 is covered by a stopper 312 fitted to contain the vacuum for a pre-determined period, typically a period in excess of the shelf life of the urine test strip. Tube stopper 312 can typically be made of an elastomer such as moldable rubber, a soft polymeric resin, silicone or any other material that is flexible, liquid impermeable, and pierceable by a needle, preferably a material that may be self-sealing to liquids after being pierced. The exact shape of the stopper is easily producible by any of many techniques known in the art, such as, but without intending to be limiting, by injection molding.

Test tube 314 contains a support 316 to which is affixed a paper urine test strip, coated or impregnated with one or more chemical reagents, here a plurality of reagents. Each reagent is reactive and identifies a different possible constituent of urine, such as glucose, bilirubin, urobilirubin, ketones, nitrites or proteins. This list is typical and not intended to be limiting. Urine test strips suitable for the assemblies of the present invention may be obtained from many commercial sources, such as Roche Diagnostics, Basel, Switzerland, and Becton Dickinson, Franklin Lakes, N.J.

Urine test strip assembly 310, also contains a trap 318, shown here as a conical trap, typically made of plastic. Trap 318 contains a small aperture typically on the order of 2-3 mm in diameter. FIG. 12C, to which reference is now made, shows a schematic isometric view of an embodiment of a urine strip containing a plurality of chemical reagents 319 affixed to a test strip support 316. The strip is somewhat recessed in support 316. Traps, other than conical traps, such as those discussed above in conjunction with microbial culturing liquid testing assemblies can also be used in conjunction with urine strip liquid testing assemblies. This includes the slow release traps discussed above.

In FIGS. 12A-12B support 316 is affixed to, or wedged against, the walls of test tube 314 using the ends 323 of support 316. Other means of joining the test strip support 316 are possible and these should be evident to one skilled in the art. The method shown in FIGS. 12A-12C is not intended to be limiting.

FIG. 12D (and FIG. 12C) shows that reagents 319 on the reagent strip are positioned in a recess on support 316. In FIG. 12D, a passageway 332 is shown running from the top of test tube 314 to its bottom, allowing drawn off urine to percolate down past reagents 319. Passage 332 is positioned between the wall of test tube 314 and support 316. The liquid then falls on and passes through trap 318 and remains at the bottom of tube 314. In order for the liquid to percolate down passageway 332 air must be displaced. Displaced air moves through apertures 325 in support ends 323 from the bottom of test tube 314 to its top.

Transfer of urine or other liquid from a collection container to urine test strip assembly 310 as in FIGS. 12A-12D is effected using a system similar to the system shown in FIGS. 1D and 1E and the discussion in conjunction therewith and therefore will not be repeated here.

Test tube 314 with stopper 312 and with urine strip support 316 affixed therein is prepared so as to be under a pre-selected vacuum. The pre-selected vacuum is empirically determined and is intended to draw off a pre-determined volume of sample from a urine sample collection container (FIGS. 1D and 1E) through a cannula 24 (FIGS. 1D and 1E). The pre-selected vacuum, and therefore the pre-selected sample volume to be drawn off, is intended to draw off a volume significantly less then the volume of tube 314.

FIGS. 12E-12H show schematic views of another embodiment of the present invention. FIGS. 12E-12H map into FIGS. 12A-12D of the previous embodiments. The difference between the embodiments is that the plurality of chemical reagents 319 positioned on a urine strip affixed to strip support 316 of FIGS. 12C and 12D are recessed on support 316; in FIGS. 12G and 12H the chemical reagents 319 are coated or embedded on a urine test strip affixed to strip support 316 and project forward from support 316. Again, there is a passageway 332 that runs the length of support 316 allowing the liquid to percolate past bottom support end 323 and down past trap 318. As above, in order for the liquid to percolate down passageway 332 air must be displaced. Displaced air moves through apertures 325 in support ends 323 from the bottom of test tube 314 to its top.

Figures 13A, 13B, 13C:
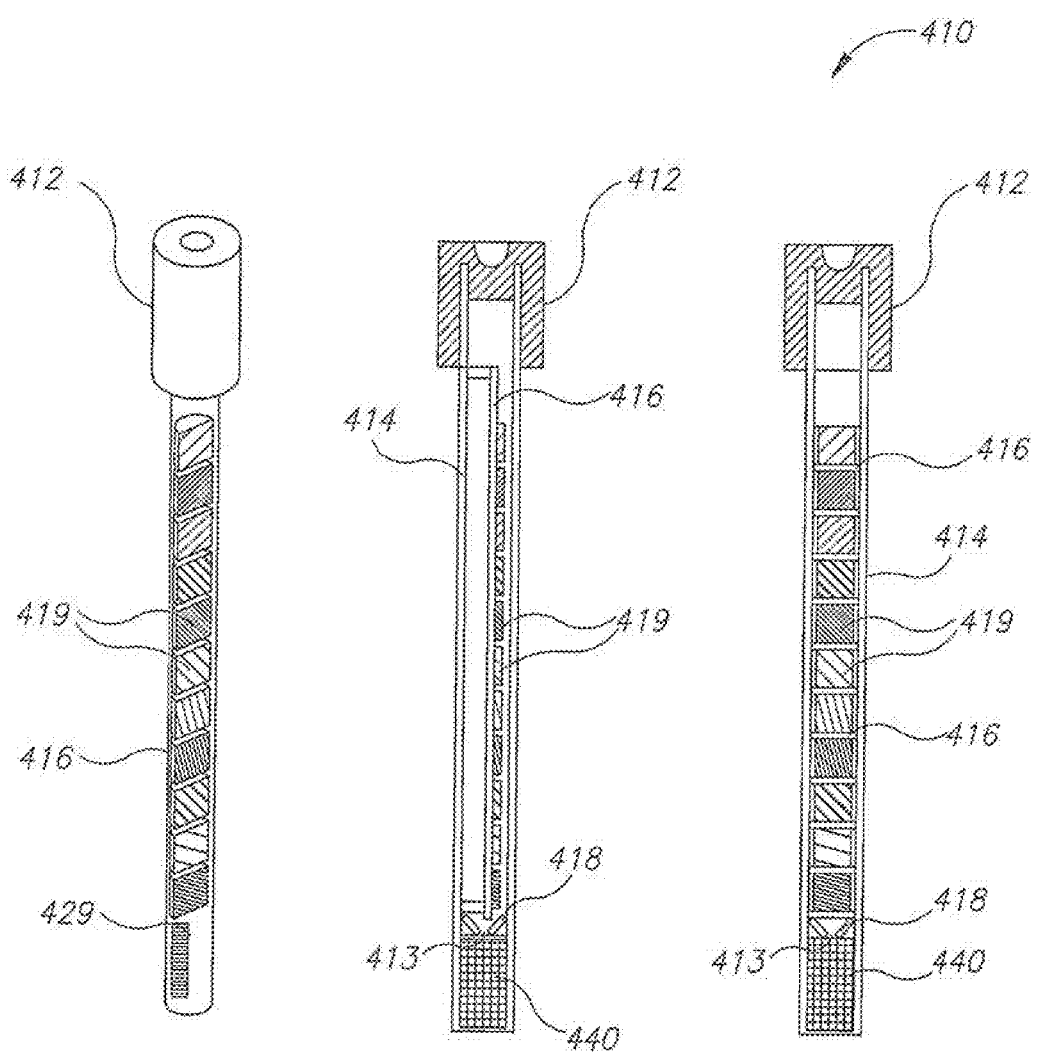
FIGS. 13A-13C are three schematic views of a third embodiment of a liquid testing assembly of the present invention using urine test strips as the source of the identifying materials.

Reference is now made to the embodiments of FIGS. 13A to 13C. The embodiment of the urine strip assembly shown in these Figures is very similar to that shown in FIGS. 12A-12H. Similar elements are similarly numbered with the introductory digit of "3" being replaced by the introductory digit of "4".

The main difference between the embodiment in FIGS. 13A-13C and 12A-12H is that there is a foam trap 440 below conical trap 418. Conical trap 418 is similar in form and construction to the conical trap discussed previously in conjunction with FIGS. 12A, 12B, 12E and 12F. As in previous embodiments, aperture 413 is formed in trap 418 and restricts liquid back flow.

Shown on the test tube of FIG. 13A is a permanently affixed printed bar code 429 which serves as a sample identification tag. It should readily be understood that while a bar code has not been shown in previous embodiments of the liquid testing assemblies discussed herein, such a bar code can be a part of any of the test tubes used in previous embodiments.

Figure 14A:
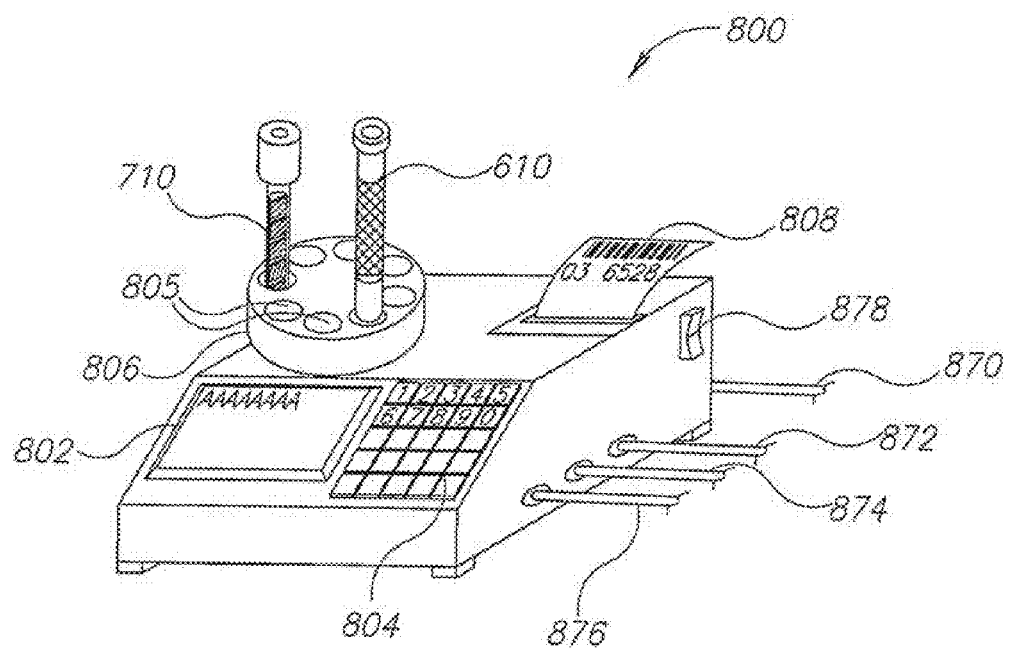
FIGS. 14A and 14B schematically show an analyzer reader which can be used with the urine strip and culture media embodiments of the present invention.
Figure 14B:
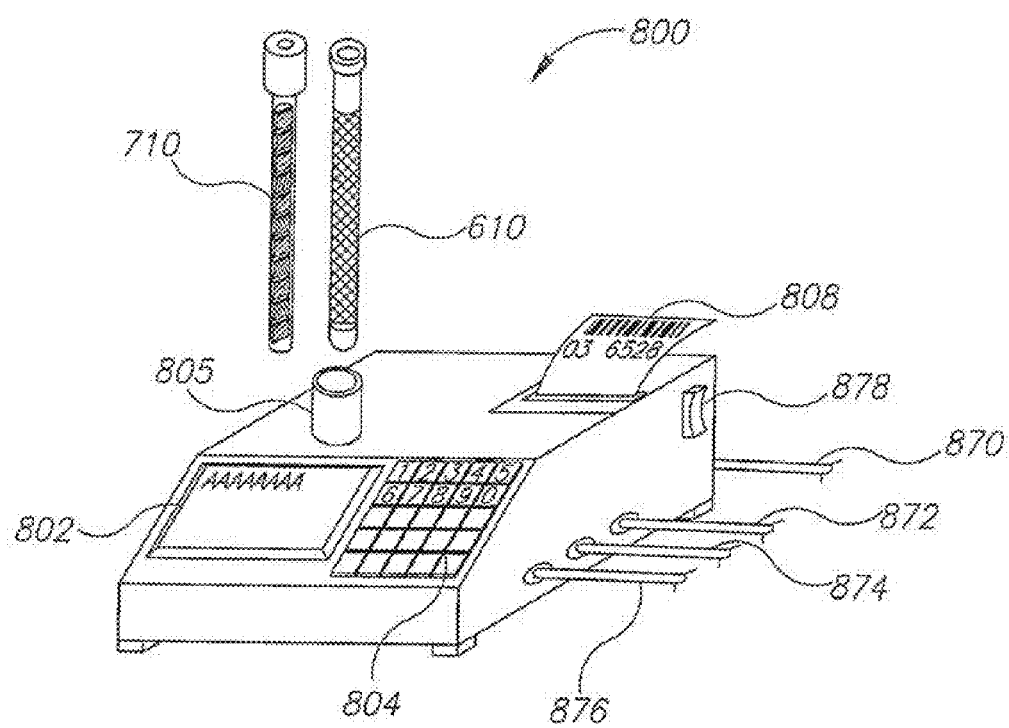
Figure 14C:
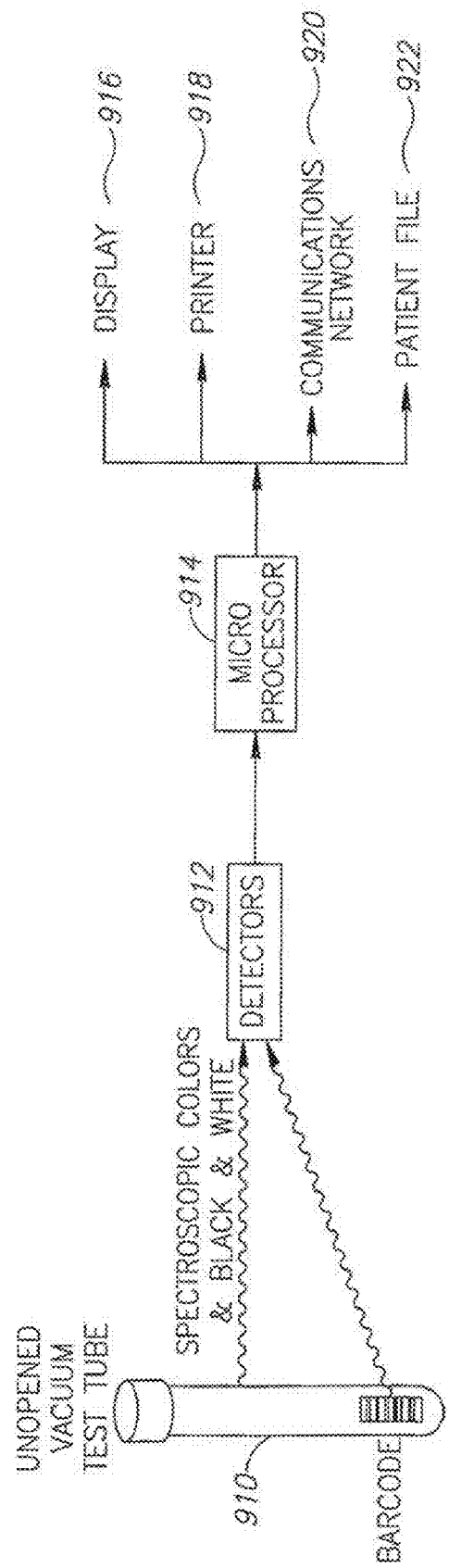
FIG. 14C shows a schematic block overview of the analyzer shown in FIGS. 14A and 14B.

Reference is now made to FIGS. 14A-14C. FIGS. 14A and 14B show embodiments of digital readers 800 that can be used to read and analyze the urine strips and/or culture media coated supports while both are still in the test tube of a liquid testing assembly constructed according to the embodiments of the present invention. Reader 800 discussed in conjunction with these Figures allows for a completely closed system after the point of urine collection from a patient into a collection cup.

In FIG. 14A, a test tube cassette 806 is shown which can rotate so that all the test tubes positioned in the plurality of tube receiving inlets 805 of cassette 806 can be brought opposite a spectroscopic detector and an optical bar code scanner (both not shown) for readings. The spectroscopic detector determines color changes in closed test tube 710 which contains a urine strip having a plurality of reagents coated or impregnated thereon. It also determines the color changes and microbial colony density on test tube 610 which contains a culture media coated support. The support has been incubated at the site of urine collection with the possibility of continued incubation at a clinical laboratory. Both test tubes 710 and 610 contain bar codes which contain patient related information and are read by the optical bar code scanner.

The receiving inlet 805 may be formed so as to have a protrusion or a slot along its side. This protrusion or slot is complementary to and mateable with test tubes constructed to include a slot or protrusion, respectively, in the test tubes side. This feature allows for the test tubes inserted into the reader's (or analyzer's) receiving inlets to be positioned in one well-defined orientation with respect to the detector of the reader or analyzer. This reduces poor readings resulting from the urine strip or culture medium being improperly aligned against the digital detector.

It should be evident to one skilled in the art that the sources of radiation and the detectors used in readers employed for urine test strip analysis may be, and typically are, different from the sources and detectors required to read color changes in culture media coated supports. Therefore, it should be evident that separate readers may be required for urine test strip analysis and analysis of culture media coated supports.

Reader 800 includes an input means 804, here a key pad, and an LCD display 802. It also contains a printer which prints the results 808 of the reading and also the bar code information. Reader 800 is activated by on/off switch 878 and is connected to a power source by connection 870. Reader 800 may also be in electronic communication with at least one of the following elements: a PC or PC network 872, a remote display 874, and a remote printer 876. While the connections here indicate wire connections to these elements, these connections may also be wireless connections.

FIG. 14B presents the same reader as in FIG. 14A, but the reader in FIG. 14B has a single test tube receiving inlet 805 instead of a rotating cassette 806 with a plurality of tube receiving inlets 805. Reader 800 in FIG. 14B operates in a manner similar to reader 800 shown in FIG. 14A.

FIG. 14C, to which reference is now made, schematically shows a description of the electronics of reader 800 and its associated system in FIGS. 14A and 14B. Detectors 912 represent: 1. an optical bar code reader and 2. at least one spectroscopic detector for determining color changes of the color bars on the urine strip and color changes in the culture media coated support on which microbial colonies have grown. Detectors 912 are well known to those skilled in the art and are readily available commercially. Measuring by the optical bar code reader and the at least one spectroscopic reader may be done concurrently or done in an alternating fashion. All readings are done directly through the walls of the test tube of the liquid testing assembly.

Spectroscopy on the culture media may be carried out using chromogenic substances added by some manufacturers to commercially available media. These chromogenic agents react with known specific microbial enzymes producing well-defined detectable color changes. From the detected color changes, qualitative and semi-quantitative determination of microbial cfus can be determined.

Not all culture media contain chromogenic substances or other agents that generate color changes detectable by visible spectrometry. In many cases with culture media, just cfu counts are made and this is often done using black-gray-white photometric readings. Appropriate photodetectors are readily available commercially for this purpose.

FIG. 14C shows a schematic block diagram of the electronics of reader 800 in FIGS. 14A and 14B. Electromagnetic radiation is received by detectors 912 which, in turn, send signals to microprocessor 914 for processing. After processing, microprocessor 914 sends information related to the detected results to at least one of the following elements: a display 916, a printer 918, a communications network or PC 920 and a patient file 922. Microprocessor 914 may analyze the data in many different ways and integrate it with previously obtained patient test results.

Since reading is done directly through the walls of the test tube of the liquid testing assembly, there is no contact with a possibly bio-hazardous liquid or wetted urine strip. Since the urine strip and/or culture media coated support does not come in direct contact with the reader when the reading is made, cleaning the reader cassette or tube receiving inlet or other parts of the reader is not required as frequently as with prior art, commercially available, readers. Generally, in prior art readers, wetted urine strips are passed directly through the reader requiring frequent cleaning to prevent contamination. Similarly, in prior art readers bar code readers are absent as identification data is not permanently affixed to the urine strips or culture media dipslides being analyzed.

The present invention also contemplates a disposable liquid testing kit. The kit comprises a liquid testing assembly as described above, a sample collection container for collecting urine from a patient, and a cannula for transferring a portion of the urine collected in the collection container to the pre-evacuated test tube or vessel of the liquid testing assembly. The liquid testing assembly may be a microbial culturing liquid testing assembly or a chemical analysis liquid testing assembly.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention. Therefore, it will be appreciated by persons skilled in the art that the present invention is not limited by what has been particularly shown and described herein above. Rather, the scope of the invention is defined by the claims that follow.

The invention claimed is:

1. A liquid testing assembly for testing a liquid, the assembly comprising:
    a test vessel having a free end and a closed end;
    a stopper having first and second ends and adapted to fit into a free end of said test vessel such that said first end faces into the interior of said test vessel, so as to substantially hermetically seal the interior of said test vessel from the ambient;
    a support coated with at least one identifying material for identifying at least one constituent of the liquid and fixed to at least one of said stopper and said test vessel, said support extending into the interior of said test vessel by a predetermined distance when said stopper is positioned in said free end of said vessel; and
    at least one liquid trap positioned proximate to the closed end of said test vessel and distal from said free end and positioned beneath said support, said liquid trap being configured, sized and operative to prevent the liquid after wetting the at least one identifying material on said support from flowing in the direction of said stopper rewetting the at least one identifying material,
    wherein said liquid testing assembly when assembled is sterilized and pre-evacuated to a predetermined low vacuum of between about 2 to about 5 inches of Hg sufficient to draw a small predetermined volume of the liquid to be sampled into said test vessel from a liquid collection container, the small predetermined volume being about 0.7 ml to about 1.5 ml, said predetermined volume being of such an amount sufficient to wet said at least one identifying material and thereafter to be substantially entirely trapped by said at least one trap, thereby ensuring identification of at least one predetermined constituent when present in the liquid and allowing visual reading of the identifying material while said support remains in said vessel.

2. A liquid testing assembly according to claim 1 wherein said at least one identifying material is at least one culture medium for culturing and determining the presence and nature of microbes present in the liquid.

3. A liquid testing assembly according to claim 2 wherein said pre-evacuated test vessel includes a pre-selected gas composition artificially introduced into said test vessel to control the rate of microbial growth.

4. A liquid testing assembly according to claim 2 further wherein said trap is positioned at a distance from said stopper greater than the distance that said culture media coated support extends into the interior of said test vessel when said stopper is positioned in said free end of said test vessel.

5. A liquid testing assembly according to claim 1 wherein said traps are selected from at least one of said group of traps consisting of: conical plastic traps, floating plastic traps, liquid absorbing traps, and hydro-gel traps.

6. A liquid testing assembly according to claim 5 wherein said liquid absorbing traps are formed of hydrophilic sponge foam.

7. A liquid testing assembly according to claim 1 wherein one of said at least one trap is a slow release trap and is positioned proximate to said free end of said test vessel and distal from said closed end of said test vessel, wherein the liquid drawn from the liquid collection container forms a reservoir on a side of said slow release trap proximal to said stopper, the liquid slowly percolating from the reservoir through said slow release trap onto said support of said assembly.

8. A liquid testing assembly according to claim 1 wherein said at least one identifying material is at least one chemical reagent for determining the presence of a chemical constituent of the liquid.

9. A liquid testing assembly according to claim 8 wherein said identifying material is a plurality of chemical reagents positioned on a urine test strip.

10. A liquid testing assembly according to claim 1 wherein said assembly further includes a means for distributing the drawn liquid, said means aiding the distribution of the drawn liquid as it passes over said identifying material coated support.

11. A liquid testing assembly according to claim 1 wherein said support is affixed in said stopper so that it is eccentrically positioned at its point of attachment relative to the center of said stopper, thereby not interfering with the insertion of a cannula which transfers liquid from the collection container to said test vessel.

12. A liquid testing assembly according to claim 1 wherein said at least one identifying material is at least one culture medium and said support has a first side and a second side and is formed to include a divider having an aperture therein and constructed so that the liquid flushes only said first side of said support, said assembly further including 1. at least one liquid trap fixedly attached to a side of said divider proximate to said at least one culture medium; 2. at least one liquid trap positioned proximate to the closed end of said test vessel and distal from said free end, said liquid trap being configured, sized and operative to receive liquid and prevent the liquid from flowing in the direction of said stopper; and 3. at least one inoculating element which after it is in contact with, and wetted by, said at least one liquid trap attached to said divider is operative to inoculate said at least one culture medium coating on said second side of said support.

13. A liquid testing assembly according to claim 12 wherein said support is coated with at least one culture medium only on said second side of said support.

14. A liquid testing assembly according to claim 13 and wherein said side of said support that lacks a culture medium is constructed as a channel to bring the liquid to said at least one liquid trap proximate to the closed end of the test vessel.

15. A liquid testing assembly according to claim 12 wherein said side of said support that includes the culture medium that is inoculated contains a track on which said at least one inoculating element travels when inoculation is effected.

16. A disposable liquid testing kit comprising:
a liquid testing assembly for testing a liquid, the assembly comprising:
a test vessel having a free end and a closed end;
a stopper having first and second ends and adapted to fit into a free end of said test vessel such that said first end faces into the interior of said test vessel, so as to substantially hermetically seal the interior of said test vessel from the ambient;
a support coated with at least one identifying material for identifying at least one constituent of the liquid and fixed to at least one of said stopper and said test vessel, said support extending into the interior of said test vessel by a predetermined distance when said stopper is positioned in said free end of said test vessel; and
at least one liquid trap positioned proximate to the closed end of said test vessel and distal from said free end and positioned beneath said support, said liquid trap being configured, sized and operative to prevent the liquid after wetting the at least one identifying material on said support from flowing in the direction of said stopper rewetting the at least one identifying material, and
a liquid collection container for collecting the liquid; and
a cannula having at least one sharpened end for piercing said stopper and transferring liquid from said container to said test vessel of said assembly,
wherein said liquid testing assembly when assembled is sterilized and pre-evacuated to a predetermined low vacuum of between about 2 to about 5 inches of Hg sufficient to draw a small predetermined volume of the liquid to be sampled into said test vessel from said liquid collection container via said cannula, the small predetermined volume being about 0.7 ml to about 1.5 ml, said predetermined volume being of such an amount sufficient to wet said at least one identifying material and thereafter to be substantially entirely trapped by said at least one trap, thereby ensuring identification of at least one predetermined constituent when present in the liquid and allowing visual reading of the identifying material while said support remains in said vessel.

17. A liquid testing system comprising:
a liquid testing assembly defined according to claim 1; and
a reader for measuring and analyzing the results of a test on the liquid, the test effected by said assembly, the reader reading and analyzing the test results by optical measurement of said identifying material coated support, while said support is positioned in said test vessel; and
said reader comprising:
at least one spectroscopic detector and a bar code reader for detecting electromagnetic radiation;
a test vessel holder wherein said holder is configured to receive at least one test vessel and said holder is positioned to allow said spectroscopic detector and said bar code reader to measure electromagnetic radiation; and
a microprocessor in electronic communication with said at least one spectroscopic detector and said bar code reader to analyze the detected radiation, the microprocessor being also in electronic communication with at least one output means operative to present the test results and patient identifying data.

18. A liquid testing system according to claim 17 wherein said output means is selected from at least one of the following group of output means: a display, a printer, a patient file and a communications network.

19. A liquid testing system according to claim 17 wherein said test vessel holder is configured to hold a plurality of test vessels when reading and analyzing test results, said test vessel holder rotatable to bring each test vessel into position for reading and analyzing by said at least one spectroscopic detector of said bar code reader.

20. A liquid testing assembly for testing a liquid, the assembly comprising:
a test vessel having a free end and a closed end;
a stopper having first and second ends and adapted to fit into a free end of said test vessel such that said first end faces into the interior of said test vessel, so as to substantially hermetically seal the interior of said test vessel from the ambient;
a support coated with at least one identifying material for identifying at least one constituent of the liquid and fixed to at least one of said stopper and said test vessel, said support extending into the interior of said test vessel by a predetermined distance when said stopper is positioned in said free end of said vessel; and at least one liquid trap positioned proximate to the closed end of said test vessel and distal from said free end and positioned beneath said support, said liquid trap being configured, sized and operative to prevent the liquid after wetting the at least one identifying material on said support from flowing in the direction of said stopper rewetting the at least one identifying material, wherein said liquid testing assembly when assembled is sterilized and pre-evacuated to a predetermined vacuum sufficient to draw a predetermined volume of the liquid to be sampled into said test vessel from a liquid collection container, said predetermined volume being of such an amount sufficient to wet said at least one identifying material and thereafter to be substantially entirely trapped by said at least one trap, thereby ensuring identification of at least one predetermined constituent when present in the liquid and allowing visual reading of the identifying material while said support remains in said vessel.

* * * * *